(12) United States Patent
Misra

(10) Patent No.: US 12,380,988 B1
(45) Date of Patent: Aug. 5, 2025

(54) SYSTEMS, METHODS, AND APPARATUSES FOR IMPLEMENTING A HOLISTIC INTEGRATED BEHAVIORAL HEALTH ENGAGEMENT PLATFORM

(71) Applicant: Elluminent LLC, Scottsdale, AZ (US)

(72) Inventor: Leesa Misra, Phoenix, AZ (US)

( * ) Notice: Subject to any disclaimer, the term of this patent is extended or adjusted under 35 U.S.C. 154(b) by 0 days.

(21) Appl. No.: 18/665,413

(22) Filed: May 15, 2024

Related U.S. Application Data

(63) Continuation of application No. 17/522,616, filed on Nov. 9, 2021, now abandoned.

(51) Int. Cl.
    *G06F 16/60* (2019.01)
    *G06F 21/62* (2013.01)
    (Continued)

(52) U.S. Cl.
    CPC ......... *G16H 20/70* (2018.01); *G06F 21/6245* (2013.01); *G06N 20/00* (2019.01);
    (Continued)

(58) Field of Classification Search
    CPC ............................ G06F 16/972; G06F 16/5846
    (Continued)

(56) References Cited

U.S. PATENT DOCUMENTS

| | | | |
|---|---|---|---|
| 2003/0200226 A1* | 10/2003 | Wells | G06F 16/972 |
| 2015/0213211 A1* | 7/2015 | Zaleski | G06F 3/0482 |
| | | | 715/753 |

(Continued)

OTHER PUBLICATIONS

Ex Parte Quayle Action for U.S. Appl. No. 17/522,616, mailed Aug. 3, 2023, 6 pages.

(Continued)

*Primary Examiner* — Baoquoc N To
(74) *Attorney, Agent, or Firm* — Elliott, Ostrander & Preston, P.C.

(57) ABSTRACT

Systems, methods, and apparatuses for implementing a behavioral health engagement platform are described herein. For example, according to one embodiment there is a method performed by a behavioral health engagement platform ("platform") having at least a processor and memory therein, in which the method includes: receiving a request at the platform from a therapist user device requesting access to the platform; generating, at the platform, a therapist GUI interface based upon the request; receiving therapist user input at the platform via the therapist GUI interface specifying a diagnostic modality for a patient, wherein content is selected by the platform based on the therapist-defined diagnostic modality; transmitting the content to a patient GUI interface for display at a patient user device; receiving patient user input at the platform from the GUI interface displayed to the patient user device, wherein the patient user input specifies one or more of: (i) selection of an avatar, (ii) responses to questions about the patient's compliance with treatment, (iii) responses to questions about the patient's emotional state and triggers before and after (iii) the viewing and rating of the platform-selected content, and (iv) biometric feedback from the patient; modifying the platform-selected content and sequence to be transmitted to the patient user device based upon the patient user input; sending the platform-selected content to the patient GUI interface at the patient user device in accordance with the sequence and modifications determined by the platform; creating alert notifications at the platform; sending the alert notification to the therapist GUI interface; and monitoring and promoting positive behavioral health outcomes. Other related embodiments are disclosed.

20 Claims, 39 Drawing Sheets

(51) Int. Cl.
     *G06N 20/00*     (2019.01)
     *G16H 10/20*     (2018.01)
     *G16H 10/60*     (2018.01)
     *G16H 20/70*     (2018.01)
     *G16H 80/00*     (2018.01)

(52) U.S. Cl.
     CPC ............. *G16H 10/20* (2018.01); *G16H 10/60* (2018.01); *G16H 80/00* (2018.01)

(58) Field of Classification Search
     USPC ........................................................ 707/805
     See application file for complete search history.

(56) References Cited

U.S. PATENT DOCUMENTS

2015/0347687 A1*  12/2015  Kallert ................ G06F 16/2379
     705/3
2017/0024547 A1*   1/2017  Bidani ................... G16H 10/20
2017/0083626 A1*   3/2017  Kensel ................ G06F 16/9577

OTHER PUBLICATIONS

Notice of Allowance for U.S. Appl. No. 17/522,616, mailed Feb. 16, 2024, 6 pages.

* cited by examiner

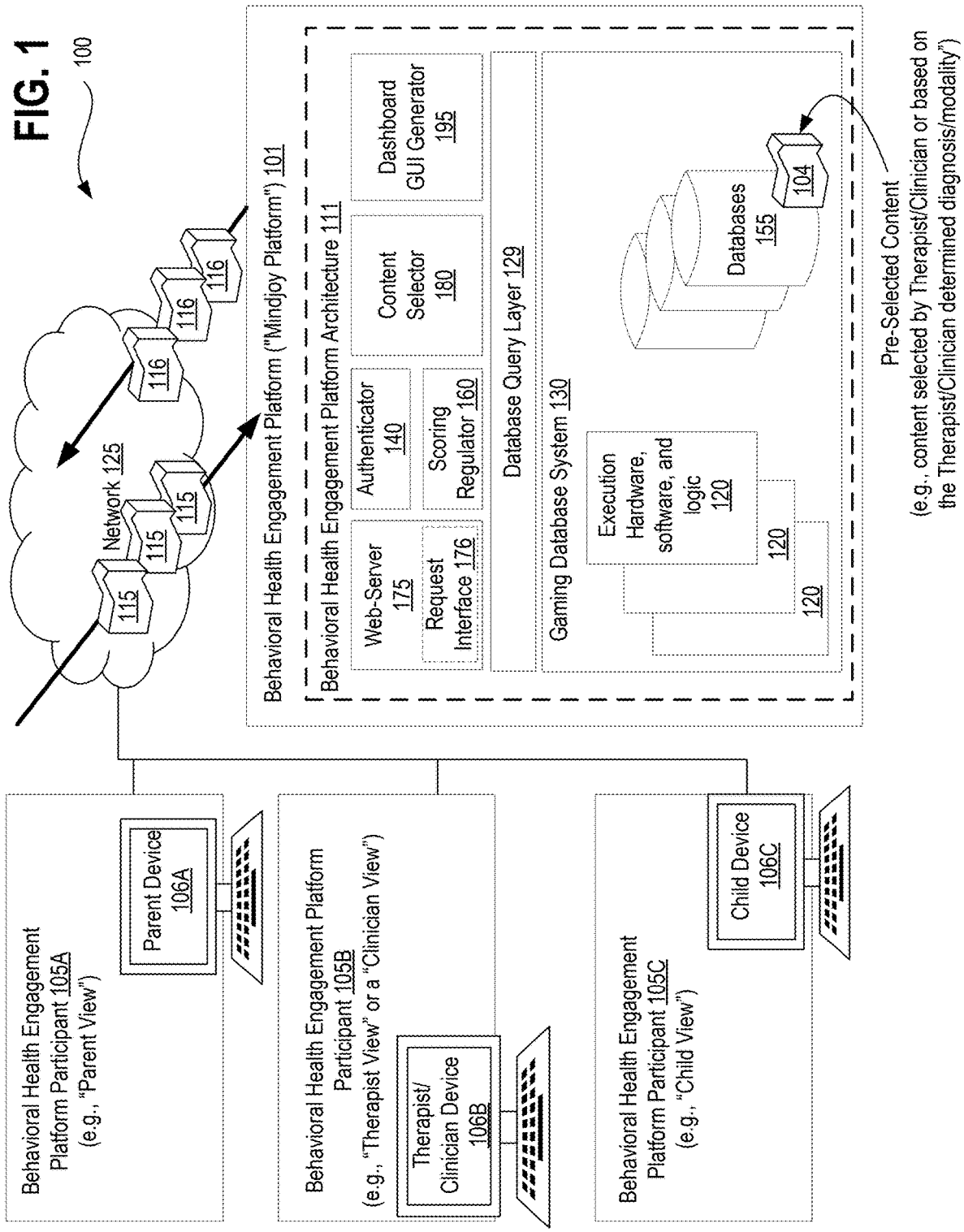

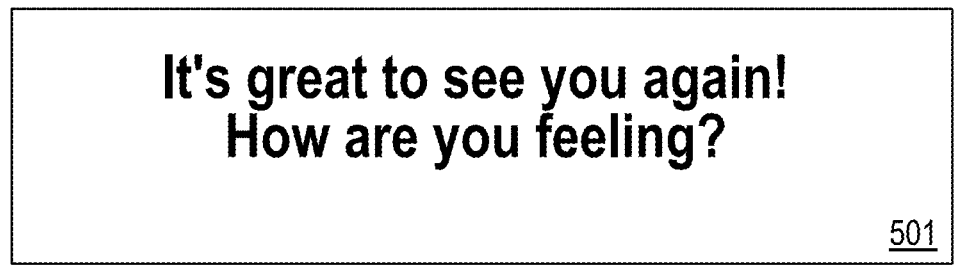
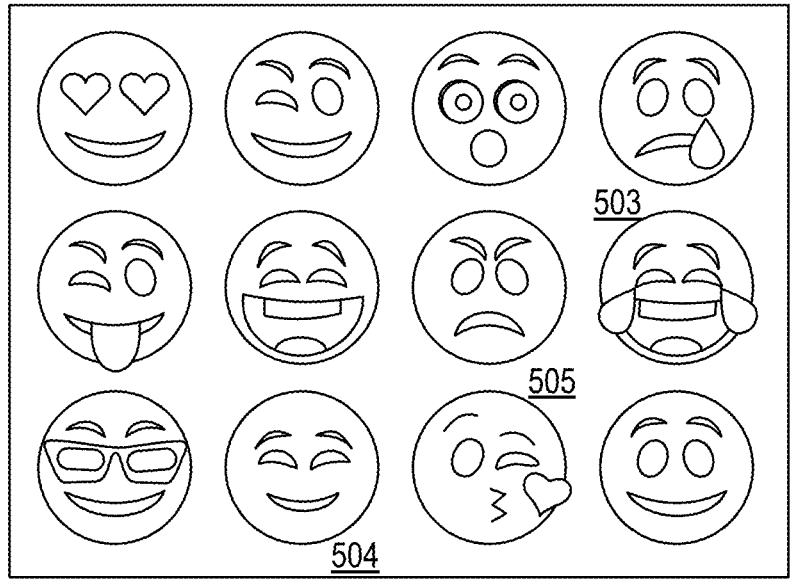
FIG. 5A

800 ⟶

I'm so sorry you're sad.
What is making you feel sad today?

801

FREE-FORM TEXT BOX 802

Since you are feeling sad, let's make you feel better by watching this. Please follow along and do the exercises for the next few minutes.
901

902

1000

Did you like the video?
1001

YES  NO
1002  1003

Still mad? Would you like to try watching this video again? 1181

YES 1182

1200
Thanks for watching! Have a nice rest of your day! 1201
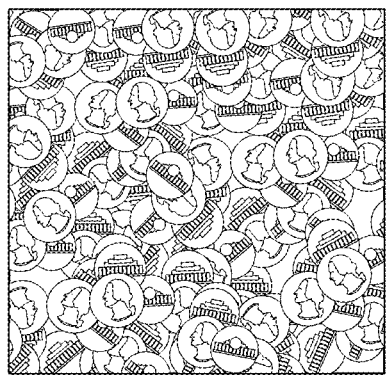
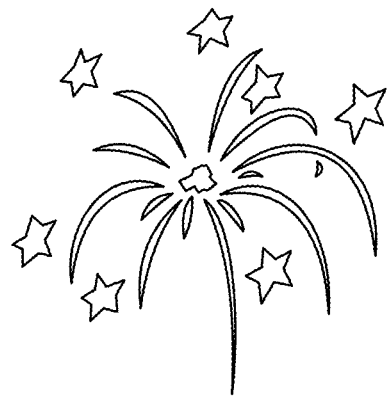
You earned___ coins today ! 1202
FIG. 12A

1220

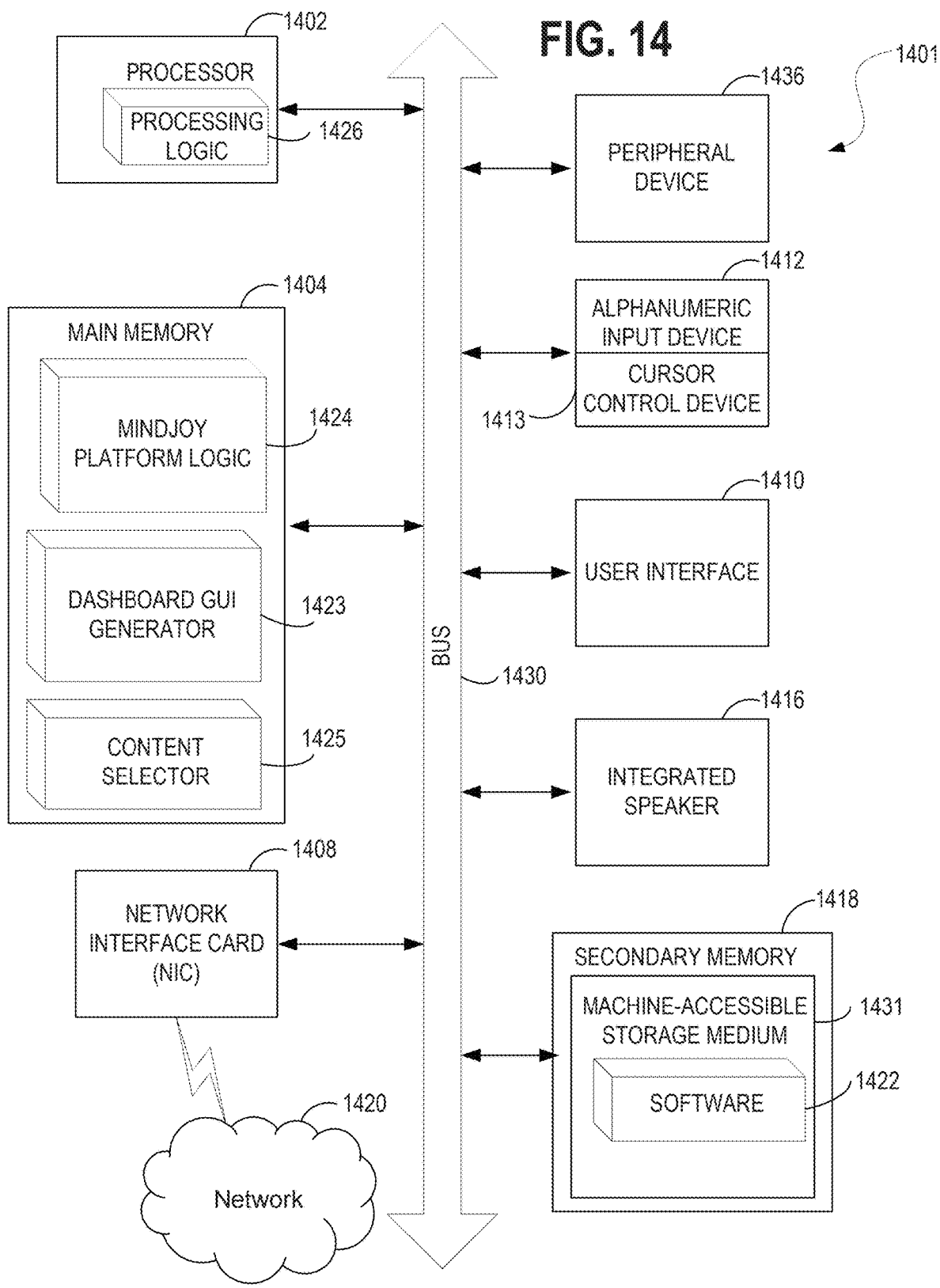

```
           ┌─────────────────┐
           │ Continued from  │
           │      15A        │
           └────────┬────────┘
                    ▼
```

Receiving patient user input at the platform from the GUI interface displayed to the patient user device, wherein the patient user input specifies one or more of: (i) selection of an avatar, (ii) responses to questions about the patient's compliance with treatment, (iii) responses to questions about the patient's emotional state and triggers before and after (iii) the viewing and rating of the platform-selected content, and (iv) biometric feedback from the patient.
1530

Modifying the platform-selected content and sequence to be transmitted to the patient user device based upon the patient user input.
1535

Sending the platform-selected content to the patient GUI interface at the patient user device in accordance with the sequence and modifications determined by the platform.
1540

Creating alert notifications at the platform based on one or more of: (i) the patient user input meeting or exceeding pre-set thresholds, and (ii) pre-set time points.
1545

Sending the alert notification to the Therapist/Clinician GUI interface for display at a Therapist/Clinician user device and a parent GUI interface for display at a parent user device.
1550

Monitoring and promoting positive behavioral health outcomes.
1555

End

SYSTEMS, METHODS, AND APPARATUSES FOR IMPLEMENTING A HOLISTIC INTEGRATED BEHAVIORAL HEALTH ENGAGEMENT PLATFORM

CLAIM OF PRIORITY

This non-provisional U.S. Utility Patent Application is a continuation of U.S. patent application Ser. No. 17/522,616, filed on Nov. 9, 2021, entitled "SYSTEMS, METHODS, AND APPARATUSES FOR IMPLEMENTING A BEHAVIORAL HEALTH ENGAGEMENT PLATFORM," the entire contents of which are incorporated herein by reference.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

Embodiments disclosed herein relate generally to the field of integrative and holistic healthcare, physical health, behavioral health, and therapy. More particularly, disclosed embodiments relate to systems, methods, and apparatuses for implementing and utilizing an integrative holistic mind body physical and behavioral health engagement platform with a vision to provide well-being for each child.

BACKGROUND

The subject matter discussed in the background section is not to be considered prior art merely because of its mention in the background section. Similarly, a problem mentioned in the background section or associated with the subject matter of the background section shall not be considered to have been previously recognized in the prior art. The subject matter in the background section merely represents different approaches, which in and of themselves, may also correspond to claimed embodiments.

In the United States, more than 75% of adults report significant stress and 19% have mental health disorders which can typically manifest with physical health symptoms triggering chronic illness from a very young age. With children ages 2 through 8 years old, the CDC reports 1 in 6 children in the US have a diagnosed mental, behavioral, or developmental disorder. For adolescents aged 9 to 17 years, as many as one in five may have a diagnosable psychiatric disorder. And yet, there is currently a shortage in a supply of child psychiatrists and psychologists throughout the country with 43 states having a severe shortage which inhibits appropriate diagnosis and care. Due to these shortages, pediatricians as well as alternative healthcare providers may seek to manage symptoms for which they may not be necessarily trained for or are working in silo without knowing the impact from other providers such as therapists, psychiatrists, speech therapists, occupational therapists, executive function coaches, or any other professional involved in the multi-systemic approach to care.

Treatment of mental health disorders accounts for the most expensive childhood medical expenditure at approximately $15 billion. The critical importance of childhood social emotional development for lifelong health and success has been confirmed by practicing psychotherapists, pediatricians and researchers. Untreated and poorly managed childhood mental health disorders have significant consequences for the child, family and the integrated healthcare system, juvenile delinquent system, child welfare and education system. It is apparent that there needs to be a paradigm shift in the overall pediatric healthcare and behavioral health system especially, given the advent of increasing mental health issues including critical shifts in the U.S. teenage suicide rate. There is a mental health crisis for teens and adolescents in the United States today.

In addition, the number of children and youth in the United States with chronic health conditions and disabilities has increased dramatically over the last fifty years—an increase of more than 400 percent. This growth has come from primarily four classes of more common, usually less complex conditions: asthma, obesity, mental health conditions, and neurodevelopmental disorders. There is an epidemiological shift among infants, children, and youth related to sociodemographic and other factors contributing to this increase. Rates of diagnosis continue to increase for other conditions such as attention deficit hyperactivity disorder (ADHD) and autism spectrum disorders, which could be related to greater awareness but evidence points to genetic origin. Genetic predisposition combined with environmental triggers or toxin exposures can cause these conditions. Other factors that could have impact are dependencies on children's social environment related to how and where children are spending their time, changes in children's diets, levels of physical activity, and media exposure (including television, computer/mobile device usage, and social media addiction) all with a variation of adult supervision can contribute to childhood adversity. A primary consideration must be given to the fact that any chronic illness (a disease that persists for a year or longer and needs ongoing medical attention limiting daily activities) risks and prevalence grows as individuals age of which severity increases when left untreated or poorly managed. These chronic illnesses can interfere with children and youth educational aspirations, future financial and economic mobility, and overall reduction in both quality and quantity of life.

In fact, cancer research has shown that the influence of prenatal and early life events can impact cancer development in adulthood. Instead of trying to find opportunities to intervene at midlife to alter or reverse disease processes that were initiated at earlier life stages, our systems and methodologies can facilitate interventions in childhood. Epigenetic alteration and genomic instability may transform or create risk factors that support proliferation of malignant cells progressing to cancer.

With the rise of global pandemics related to viruses (e.g., Covid-19) and other infections, consideration to the threat of life in children with chronic disease should also be given. In cross-sectional studies children that had a Covid-19 diagnosis for inpatient encounters or ED visits, the most commonly documented underlying conditions were asthma, neurodevelopmental disorders, anxiety and fear-related disorders, depressive disorders, and obesity.

The healthcare system was created to treat illness and focus on body parts dividing medical specialties to work on one issue at a time. Mindjoy facilitates the holistic healthcare model so that each child can maintain optimal health and well-being using an integrative multi-systemic collaborative care approach, preventative health objectives, patient-centric care through precision medicine in detection and diagnosis, managing personalized treatment plans and outcomes in real time by understanding molecular diagnostics, epigenetics and biofeedback along with subjective reporting.

Studies such as those conducted by the Anxiety and Depression Association of America have shown that solely relying on drugs to manage behavioral health disorders without other interventions causes the disorders to simply linger or exacerbate, requiring increased use of medication and higher drug dosage. In addition, the lack of any behavioral therapy intervention creates dependence and the client will not be able to develop tools for managing his or her symptoms without medication.

Traditional behavioral health therapy and pediatric care involves periodic interaction between a child and therapist in the form of therapy sessions or child with pediatrician in the form of primary care visits, with often limited communication and involvement from other parties such as the child's parents due to privacy concerns or cost and time factors.

Problematically, tracking therapeutic efficacy (the therapeutic effects and benefits of psychotherapy treatments) in real time among children diagnosed with mental health disorders is a challenge for therapists. Lack of adherence and compliance to psychotherapy techniques and treatments in both children and adults as well as compliance in medication management further exacerbates this problem and makes it challenging to promote positive behavioral health outcomes. There is also a lack of any existing comprehensive system for children that provides one central health management platform integrated with an EHR/EMR that is data driven with a unified treatment plan that can be shared across multiple clinicians combining therapeutic care using evidence-based wellness practices with traditional allopathic medicine. The present state of the art may therefore benefit from the systems, methods, and apparatuses for implementing and utilizing an integrative behavioral health engagement platform as is described herein.

BRIEF DESCRIPTION OF THE DRAWINGS

Embodiments are illustrated by way of example, and not by way of limitation, and will be more fully understood with reference to the following detailed description when considered in connection with the figures in which:

FIG. 1 depicts an exemplary architecture in accordance with described embodiments;

FIG. 5A depicts an exemplary emotional state selection view, in accordance with described embodiments;

FIG. 8A depicts an exemplary emotional source trigger free-form text response view, in accordance with described embodiments;

FIG. 10 depicts an exemplary post-behavioral therapy video presentation binary rating view, in accordance with described embodiments;

FIG. 11E depicts another exemplary post-behavioral therapy video presentation binary repeat selection view, in accordance with described embodiments;

FIG. 12A depicts an exemplary session completion and point total reporting view, in accordance with described embodiments;

FIG. 14 illustrates a diagrammatic representation of a machine in the exemplary form of a computer system, in accordance with one embodiment; and FIGS. 15A and 15B depict flow diagrams illustrating a method for implementing and utilizing a behavioral health engagement platform, in accordance with disclosed embodiments.

DETAILED DESCRIPTION

Figure 2A:
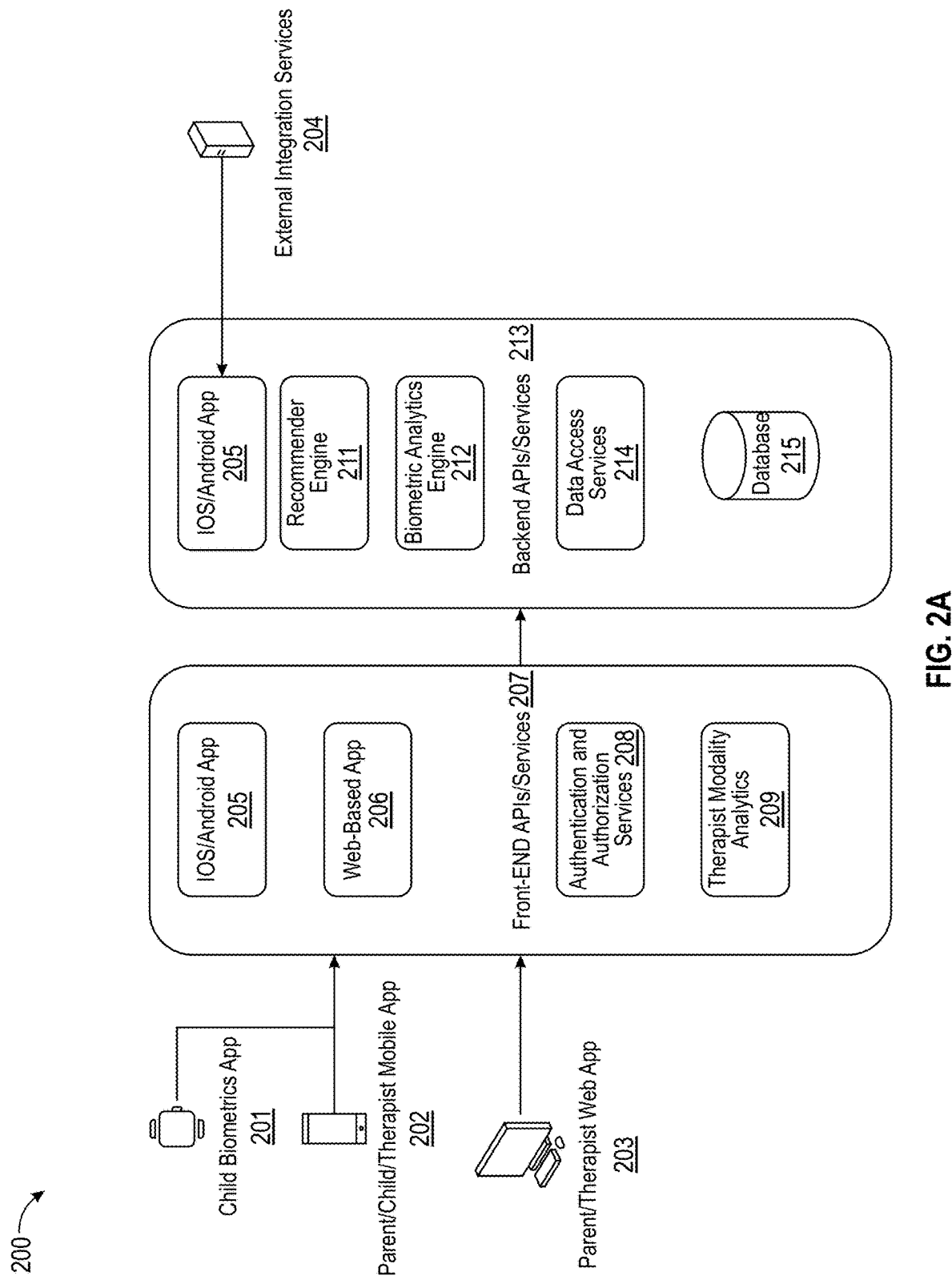
FIG. 2A illustrates an exemplary computing architectural diagram in the exemplary form of software applications and associated architecture, in accordance with one embodiment.

Described herein are systems, methods, and apparatuses for implementing and utilizing an integrative behavioral health engagement platform.

The most common childhood mental health disorders are ADD/ADHD, autism, anxiety, depression and disruptive behavior disorders. A mobile app for management of these specific diagnoses can alleviate barriers such as stigma, availability, and financial constraints.

Various behavioral health interventions and exercised are used to modify behaviors causing behavioral health conditions such as depression and anxiety in children. An example of this is Eye Movement Desensitization and Reprocessing (EMDR) therapy for trauma victims which desensitizes the child patient's response to negative memories and stimuli through visualization, relaxation techniques, eye movements, and forging new associations between the memory of the traumatic event and the child's reaction to it.

Many recent publications in psychology have called for digital interventions in therapy to increase availability, accessibility and cost-effectiveness which has resulted in the production of several mental health applications specifically on a mobile device due to the ubiquitous usability of the platform. Due to the pervasive use of smartphones, mental health applications can now disseminate information in real time promoting positive behavioral change.

As therapy often involves changing conditions, restrictions on follow-up frequency due to scheduling and cost may not allow a therapist/clinician to be fully apprised of changes in a child's behavioral health or to grasp a full understanding of treatment outcomes with CBT, DBT, ACT, EMDR and other treatments. In addition, intake and follow-up questionnaire forms are often not taken regularly only periodically either annually or biannually to evaluate child events such as outbursts and bed-wetting.

As noted above, there is a need for improved systems and methods for the delivery, tracking, and reporting on the efficacy of mental health treatment, especially with respect to the mental and behavioral health care of children due to the established conventions in the healthcare system of periodic interaction between a child and therapist in the form of therapy sessions with limited to no communication or involvement from other parties such as the child's parents, pediatrician, psychiatrist and additional providers.

Unfortunately, there is often little time for parents to learn about their child's progress from the therapist during a therapy session as such interactions takes away from time between the therapist and the child. Because behavioral therapy can be expensive, it is often too costly for parents to schedule a separate session to meet with the therapist. As a result of these constraints, parents are affected as well and may often feel disconnected with their child's therapy process, with little idea of what goes on in therapy, as well as how effective therapy is for their child.

Not only is the tracking of therapeutic efficacy practically impossible with prior known systems, presenting a systemic challenge for therapists, these issues are further exacerbated due to the common lack of adherence and compliance to psychotherapy techniques and treatments in both children and adults. These issues make it challenging to promote positive behavioral health outcomes in patients of any age.

For instance, patients may find therapeutic intervention techniques too difficult to recall or do not understand how the technique is performed. Recall bias can also be a problem when children do not remember what emotions they were feeling when there was an incident, if and when they used the technique, and whether or not the technique helped. Also, because the youngest of children are often limited in how they can expand on their feelings, parents often assume the role of describing their child's responses and feelings towards therapy to the therapist. Thus, more direct communication is needed between therapists and child patients of the youngest ages, such as those around five years old, in order to minimize the subjective filter of parental opinion driving the description of the child's emotional through verbal or written subjective reporting, resulting in incomplete or inaccurate source data for the therapist to make assessments based off of. There is also a lack of any integrated model between other healthcare providers, therapists and parents to notify them of a child's ongoing behavioral health condition, determine if medication or physical symptoms are contributing to the issues.

Finally, therapists and other healthcare practitioners often write down their assessments in the form of free-form notes without standardization or metrics which makes outcomes tracking and reporting for insurance purposes difficult.

An integrative behavioral health engagement platform (the "Mindjoy Platform") is thus described herein which may be utilized by therapists, parents, healthcare providers and children which provides the opportunity for the child patient to report changes in their behavior and overall health in real time to these various parties and to promote engagement between the various parties outside of therapy sessions. Children may report their emotional state with triggers elicited in real-time to minimize recall issues, as well as being provided a self-help resource through pre-selected content such as videos displayed to them to help them cope with behavioral health episodes. Therapists/clinicians may also input compiled information from these various parties into the platform and standardize their assessment process to quantify and track the efficacy of the behavioral therapies they utilize through various metrics including biometric data from the child. Modifications in therapy such as variations in therapeutic exercise sequence or medication changes may also be implemented, as will be described in greater detail below. For instance, utilizing collected biometric and biosensor data, the platform implements continuous monitoring and detection of stressful events from a compatible device, such as a commercial wrist worn device (enabled to capture and provide biometric data) to assist in mental health and well-being self-management by developing a stress-detection application as part of a mobile app. Other devices may be similarly enabled, such as a specially configured tablet, smart phones, cameras, dedicated sensory devices coupled with computing equipment (e.g., such as a dedicated oxygen sensor or heart rate monitor), and so forth. Still further, mobile phone data may be consumed and analyzed by the platform. For example, self-reported mental health and nervous system conditions may be collected within different data collection time windows and then analyzed and utilized identify effective (e.g., the least disruptive) time window for actively collecting mobile-health data with high degree of accuracy.

According to certain embodiments, sensors generally including biometric sensors are enabled to detect and report to the platform various attributes of the patient. Such resulting biometric data includes secretions such as sweat which, as noted elsewhere, may be utilized to monitor the health of the patient, as well as other physiological parameters of the patient such as oxygen levels, heart rate, temperature, and so forth. For instance, biomarkers may be detected by the sensors and determinable by the platform based on such biometric data, thus enabling for more comprehensive integration with overall health of the patient. Sensory data indicative of biomarkers has been shown to directly correlate with actual biomarkers determinable from, for instance, blood samples and analysis for the same patient. These biomarkers include, but are not limited to, glucose, sodium, lactate, potassium, and protein detectable in the human secretions. Such detection means may similarly include the presence of chloride ions which may be indicative of, for example, cystic fibrosis, thus triggering the system to raise a flag, alert, or prompt to the clinician for further human review. In other embodiments, the platform may prompt the patient directly for certain determinable patient states, such as to remind a patient to take a medication or to advise the patient of abnormal biometric indicators with a suggestion to, for instance, drink a glass of water.

Through the use of wearable sensor technology, more inclusive and comprehensive health outcomes are made possible, including the real-time monitoring of a patient's health in all aspects, and not just limited to psychological health. Such embodiments thus enable, by way of analogy, a "thermometer" or "temperature gauge" type real-time reading for the human body, but specific to other biomarkers besides merely temperature.

The platform allows parents and therapists to have more open and frequent communication, for example, by parents reporting information to therapists via questionnaires ahead of therapy sessions with the child instead of using valuable time during therapy sessions to do so. Therapists and parents may also receive alerts when the child reports a threshold of consecutive negative emotions over a period of sessions in which the child uses the platform ("platform sessions"), in contrast to live or virtual clinical sessions between the child and the therapist ("therapy sessions"). Validation of child reported data may also be accomplished through biometric feedback from devices such as smart watches measuring, for example, the heart rate, pulse and breathing rate of the child. Third parties such as insurance companies may also use the reported metrics that the platform provides for coverage and billing purposes. Researchers may also use permitted aggregate data from groups of children using the platform for clinical and epidemiological studies.

The integrative behavioral health engagement platform can improve the overall behavioral health system by minimizing access barriers for families seeking treatment, assisting primary care pediatricians to monitor therapy results as a part of their practice, tracking compliance and usage of therapeutic techniques such as triadic mode of therapy where therapists work with children and parents to incorporate parenting skills and relationship training, education, and family therapy while keeping all clinicians involved in the care of the child updated.

For instance, according to a particular embodiment, there are means for implementing and utilizing a behavioral health engagement platform. For example, according to one embodiment there is a method performed by a behavioral health engagement platform ("platform") having at least a processor and memory therein, in which the method includes: receiving a request at the platform from a therapist user device requesting access to the platform; generating, at the platform, a therapist GUI interface based upon the request; receiving therapist user input at the platform via the therapist GUI interface specifying a diagnostic modality for a patient, in which content is pre-selected based on the pre-defined diagnostic modality; transmitting the content to a patient GUI interface for display at a patient user device; receiving patient user input at the platform from the GUI interface displayed to the patient user device, in which the patient user input specifies one or more of: (i) selection of an avatar, (ii) responses to questions about the patient's compliance with treatment, (iii) responses to questions about the patient's emotional state and triggers before and after (iii) the viewing and rating of the pre-selected content, and (iv) voice/facial recognition and biometric feedback from the patient; modifying the pre-selected content including content sequence based upon the patient user input; sending the modified pre-selected content to the patient GUI interface at the patient user device; creating alert notifications at the platform based on one or more of: (i) the patient user input meeting or exceeding pre-set thresholds, and (ii) pre-set time points; sending the alert notification to the therapist GUI interface for display at a therapist user device and a parent GUI interface for display at a parent user device; and monitoring and promoting positive behavioral health outcomes.

In the following description, numerous specific details are set forth such as examples of specific configurations, use cases, materials, components, etc., in order to provide a thorough understanding of the various embodiments. It will be apparent, however, to one skilled in the art that these specific details need not be employed to practice the embodiments disclosed herein. In other instances, well-known materials or methods have not been described in detail in order to avoid unnecessarily obscuring the disclosed embodiments.

In addition to various hardware components depicted in the figures and described herein, embodiments further include various operations described below. The operations described in accordance with such embodiments may be performed by specially manufactured components or may utilize general-purpose components in certain instances to realize and perform the innovative function and configuration of the described embodiments. Alternatively, the operations may be performed by a combination of customized specially manufactured components with certain general purpose components to make, use, and practice the inventive aspects as set forth herein.

FIG. 1 depicts an exemplary architecture 100 in accordance with described embodiments.

In one embodiment, a behavioral health engagement platform architecture 111 is communicably interfaced with a plurality of user devices 106A-C (e.g., such as mobile devices, smart phones, tablets, PCs, etc.) through behavioral health engagement platform ("Mindjoy Platform") 101. The behavioral health engagement platform 101 is communicably interfaced with the user devices 106A-C via Network 125, for instance, over the public Internet. Behavioral health engagement platform participants 105A-C associated with each of the user devices 106A-C make take on different roles for any given session instance. For example, behavioral health engagement platform participant 105A is referred to here as the "parent view," but may take on a different role in other session instances managed by the behavioral health engagement platform 101. Similarly, behavioral health engagement platform participant 105B is referred to as the "therapist view," and behavioral health engagement platform participant 105C is referred to as the "child view." The "parent view" may, for example, include the number of reward points a child has earned, the number and dates of the child's entries, video content viewed, sleep patterns, diet tracking, and emotional state but not details about emotional triggers.

Due to client confidentiality and privacy, parents will not be notified in entirety as far as sources of triggers unless and until it is necessary for mandatory reporting. States require a therapist to contact authorities if a patient is a danger to him/herself, to others, and/or if the therapist suspects that a known child is being abused. These reporting laws can vary slightly by each state but they are explained to all parents/guardians of children who are enrolled in professional counseling and this limitation of confidentiality is critical application to any individual receiving medical care or mental health services including the application disclaimer notice.

For example, the behavioral health engagement platform 101 may govern and enforce certification with various government regulations, mandates, and confidentiality requirements, including HIPAA and COPPA.

For instance, HIPAA compliance is pursuant to is the Health Insurance Portability and Accountability Act of 1996 which is a United States federal statute signed into on Aug. 21, 1996. HIPAA modernizes the flow of healthcare information, stipulates how personally identifiable information maintained by the healthcare and healthcare insurance industries should be protected from fraud and theft, and addressed some limitations on healthcare insurance coverage. Further still, HIPAA generally prohibits healthcare providers and healthcare businesses from disclosing private information to anyone other than a patient and the patient's authorized representatives. HIPAA does not restrict patients from receiving information about themselves, prohibit them from voluntarily sharing their private health information however they choose, or—if they disclose private medical information to family members, friends, or other private individuals—legally require those non-covered people to maintain confidentiality.

With regard to COPPA compliance, COPPA provisions are enforced pursuant to the Children's Online Privacy Protection Act of 1998 which is a United States federal law, enacted Oct. 21, 1998 and made effective on Apr. 21, 2000. COPPA applies to the online collection of personal information by persons or entities under U.S. jurisdiction about children under 13 years of age including children outside the U.S., if the company is U.S.-based. COPPA details what a website operator must include in a privacy policy, when and how to seek verifiable consent from a parent or guardian, and what responsibilities an operator has to protect children's privacy and safety online including restrictions on the marketing of those under 13.

In one embodiment, the behavioral health system 130 includes databases 155 which store relevant platform data in compliance with federally mandated statutes, including HIPAA and COPPA. For example, such databases may store tables, datasets, and underlying database records with user data, platform settings, pre-selected content, rewards points systems, etc., on behalf of behavioral health engagement platform participants 105A-C (e.g., parents, therapists, children, other healthcare providers, etc., utilizing the behavioral health engagement platform 101) in a manner which enforces the relevant statutory and compliance mandates.

Behavioral health system 130 includes a plurality of underlying hardware, software, and logic elements 120 that implement database functionality and a code execution environment within the behavioral health engagement platform 101. In accordance with one embodiment, behavioral health system 130 further implements databases 155 to service database queries and other data interactions with the databases 155 in support of the behavioral health engagement platform as described herein. The hardware, software, and logic elements 120 of the behavioral health system 130 are separate and distinct from a plurality of behavioral health engagement platform participants (105A, 105B, and 105C) which utilize the services provided by the behavioral health engagement platform 101 by communicably interfacing to the behavioral health engagement platform 101 via network 125. In such a way, behavioral health engagement platform 101 may implement on-demand behavioral health tracking and outcome promotion, on-demand database services in support of the behavioral health engagement platform, or cloud computing services implementing the behavioral health engagement platform on behalf of behavioral health engagement platform participants 105A-C.

According to particular embodiments, the behavioral health engagement platform 101 integrates and communicates with EHRs/EMRs (e.g., via public facing APIs or proprietary APIs) as well as Vimeo or Envato video repository databases, AI chatbot and text/SMS messaging platforms. According to alternative embodiments, the behavioral health engagement platform 101 further integrates and communicates with retail sites.

As shown here, the behavioral health engagement platform 101 receives input and other requests 115 from a plurality of behavioral health engagement platform participants 105A-C via network 125 (such as the public Internet). For example, incoming platform interactions and events (such as invitations from the therapist to the parents/child and invitation acceptance events by the child, etc.), API requests for support GUI interfaces executing at the variously depicted user devices and more particularly, interactions with displayed graphical user interfaces and displays transmitted to each of the parent device 106A, the therapist device 106B, and the child device 106C. Other inputs may be received from the behavioral health engagement platform participants 105A-C to be processed against the behavioral health system 130 via the behavioral health engagement platform architecture and its various sub-systems. In certain embodiments, the inputs and requests 115 from the behavioral health engagement platform participants 105A-C may include setting selections, acceptance of default settings or request for non-default options, scoring systems and scoring settings, pre-selected content settings and parameters, all of which is to be hosted, stored, and executed within the behavioral health engagement platform 101 on behalf of such behavioral health engagement platform participants 105A-C. In such embodiments, responses 116 from the behavioral health engagement platform 101 may constitute data records, reports, analytics, charts, GUI displays to be presented at the user devices, confirmation of pre-selected content, scoring, and session settings by the behavioral health engagement platform 101, or other information in support of the of behavioral health engagement platform as described herein, or may be some combination thereof.

According to certain embodiments, the behavioral health engagement platform 101 hosts, manages, and provides both a knowledge base and an internal repository or database of video content. In alternative embodiments, the behavioral health engagement platform 101 leverages a network of videos and video content which may include video content stored and hosted by the behavioral health engagement platform 101 as well as third party provided and third party hosted video content.

In one embodiment, each behavioral health engagement platform participant 105A-C is an entity or user from the group consisting of: a child, a therapist, a parent, that registers with the online behavioral health engagement and cloud computing services provided by the behavioral health engagement platform 101.

In one embodiment, requests 115 are received at, or submitted to, a web-server 175 within behavioral health engagement platform 101. The behavioral health engagement platform 101 may receive a variety of requests for processing by the behavioral health engagement platform 101 and its administration of behavioral health engagement sessions as described herein in conjunction with use of behavioral health system 130. Incoming requests 115 received at web-server 175 may specify which scoring, pre-selected content, and other configurable settings (e.g., such as displays, users, etc.) are to be applicable for any particular behavioral health engagement session which are then implemented by behavioral health engagement platform 101 as a series of query requests, search requests, status requests, database transactions, graphical user interface requests and interactions, processing requests to retrieve, update, or store data on behalf of one of the behavioral health engagement platform participants 105A-C, code execution requests, and so forth, in support of the behavioral health engagement platform as described herein.

Web-server 175 may be responsible for receiving requests 115 from various behavioral health engagement platform participants 105A-C via network 125 and provide a web-based interface or other graphical displays to a user device 106A-C or machine originating such data requests 115.

The behavioral health engagement platform 101 may implement a request interface 176 via web-server 175 or as a stand-alone interface to receive requests packets or other requests 115 from the user devices 106A-C. Request interface 176 further supports the return of response packets or other replies and responses 116 in an outgoing direction from behavioral health engagement platform 101 to the user devices 106A-C. Response packets and responses 116 sent from the behavioral health engagement platform to the variously connected user devices 106A-C may constitute a variety of responses 116, such as acknowledgments of receipt (e.g., where no action is taken but confirmation of a request is nevertheless provided) or other interactive responses such as the return of data responsive to a query, generation and presentment of GUI interfaces or other UX/UI and graphical overlays generated by the behavioral health engagement platform and pushed to the user devices (e.g., the parent device 106A, the therapist/clinician device 106B, and the child device 106C) for display, authentication challenges, sponsored advertising content, etc. The displays at user devices 106A-C may be customized to show select content depending on the user device. For example, parent user device 106A may not display content regarding the details of child patient's responses to behavioral health episode triggers, which may be appropriate in situations when, for example, the child patient identifies the parent as being the trigger.

In certain embodiments, a client-server architecture may be utilized in which the behavioral health engagement platform operates upon servers controlled by a particular organization, such as a behavioral health center clinic, residential treatment centers, pediatric clinic and hospitals. In such an implementation, it may be desirable that communications between user devices 106A-C and the behavioral health engagement platform architecture are transported via a WAN, LAN, WLAN, VPN, or other more restrictive communications network when compared with transport via the public Internet. Regardless of the networking architecture, interactions between the behavioral health engagement platform architecture 111 and the communicatively interfaced user devices 106A-C would remain fundamentally the same.

Further depicted here is an authenticator 140 which operates on behalf of the behavioral health engagement platform 101 to verify, authenticate, and otherwise credential behavioral health engagement platform participants 105A-C (e.g., via their respective user devices 106A-C) attempting to gain access to the behavioral health engagement platform 101 and its services.

Scoring regulator 160 operates to capture and implement the manner by which points are awarded, accumulated, tracked, and calculated. The content selector 180 operates to locate, retrieve, and transmit to the child device 106C the custom or template based multi-media content for consumption by the child patient. These selections may be based on settings specified by the therapist or these selections may be based on the therapist having specified a diagnosis or modality for the child patient, in which the system then selects the appropriate content based on, for example, machine learning algorithms, therapist specified criteria, behavioral health engagement platform ("Mindjoy Platform") 101 specified defaults, etc. The content selector may further operate to determine implementation of behavioral health engagement platform default options and settings or a configurable and permissible variation of platform options and settings for any given behavioral health engagement platform session hosted and facilitated by the behavioral health engagement platform 101. The Dashboard GUI Generator 195 operates to both generate GUIs for transmission to remote computing devices (e.g., such as the parent device 106A, the therapist device 106B, and the child device 106C) as well as to interface with the request interface 176 to capture user specified inputs from the various remote computing devices (e.g., such as the parent device 106A, the therapist device 106B, and the child device 106C). For example, the therapist may enter settings at the therapist device 106B via a GUI generated and transmitted by the dashboard GUI generator. Similarly, the parent may observe a parent dashboard to check on the status of therapy for the child or to schedule appointments or to correspond electronically with the therapist, etc. Still further, the child may interact with a child GUI transmitted to the child device 106C from the dashboard GUI generator 195 which permits the child to interact with various interactive media and content as specified by the therapist or interact with content selected by the platform's consent selector 180 based on a therapist determined diagnosis or modality, etc.

According to a particular embodiment, the behavioral health engagement platform 101 implements a two way video interface for virtual therapist appointments and further records those therapy appointments for viewing later, as needed. For example, Augmented Reality/Virtual Reality (AR/VR) technology may be utilized or the behavioral health engagement platform 101 may be integrated with an AR/VR platform that would also reflect and capture data related to elevated biometrics of the child/patient during a session, thus correlating those biometrics temporally (e.g., synchronized in time) with the session, such as when the child is discussing specific subject matter. For instance, certain embodiments may incorporate the recording and archiving of both audio and video from in-person as well as virtual therapy visits, such that the captured data may then be analyzed to improve future treatment by automatically evaluating interviewing skills of psychotherapists on the basis of the recordings from live and virtual sessions. In so doing, it is expected that such a feedback loop (e.g., capturing the sessions, analyzing the sessions, and providing input to the therapist/clinician based on the session) will ultimately provide improved skill development and retention for better patient outcomes.

The dashboard GUI generator 195 may further operate to capture input selections, and coordinate implementation of a session specified or session required display (e.g., such as child display, therapist/clinician display, parent display, etc.) for use with respect to any given behavioral health engagement platform session hosted and facilitated by the behavioral health engagement platform 101.

The integrated behavioral health engagement platform may be presented as an online website by the behavioral health engagement platform 101 for engagement with a group of other participants (such as other healthcare providers) in tracking and promoting positive behavioral health outcomes.

Certain embodiments described herein relate to an integrative behavioral health engagement website with clinical data and health outcomes tracking properties as implemented and facilitated by the behavioral health engagement platform 101. Such disclosed embodiments may be applied to many different behavioral health diagnosis and treatment modalities for conditions such as anxiety, depression, attention deficit/hyperactivity disorder (ADHD), behavioral disorder, obsessive compulsive disorder (OCD), and post-traumatic stress disorder (PTSD). Furthermore, the embodiments may be applied to a variety of patients at any level from individual patients to groups of patients and at any stage of therapy from initial diagnosis to resolution, maintenance, and remission. The embodiments allow children, therapists, parents, other healthcare providers and school staff to contribute behavioral health data for tracking and analysis to promote positive behavioral health outcomes, implemented and facilitated by a behavioral health engagement platform 101.

Disclosed embodiments provide system implemented means (e.g., via the behavioral health engagement platform architecture 111 of the behavioral health engagement platform 101) for a behavioral health engagement platform involving the child, parents, therapists, other healthcare providers, and other parties such as school staff to contribute and track information regarding the behavioral health of the child. Furthermore, users may be notified of symptoms or episodes of the child's behavioral health warranting their attention. Further still, pre-selected content may be modified and displayed to the child based on user provided input data, with interactions controlled and facilitated by the behavioral health engagement platform.

According to particular embodiments, the behavioral health engagement platform participant having the role of "therapist" invites other behavioral health engagement platform participants 105A-C via the behavioral health engagement platform 101. In such an example, a session begins after parents are invited to fill out a questionnaire regarding the child's characteristics (such as the child's age, diagnosis, and treatment modality), and the child user is authenticated, for example by biofeedback, voice or facial recognition software.

For example, through the capture of mobile app data, it is further possible for questionnaires to be distributed in order to better understand mental health development and similarly to improve and identify the most significant psychological symptoms in a specific diagnosis.

FIG. 2A illustrates an exemplary computing architectural diagram in the exemplary form of software applications and associated architecture 200, in accordance with one embodiment.

For example, the behavioral health engagement platform 200 may be accessed by the child patient on an IOS/Android app 205 via a smartphone/tablet or a web-based app 206 via a computer or laptop. A specially configured interface may also receive biometric input into the child biometrics app 201 which may be connected to a biometric monitoring device, such as a smart watch that the child patient wears which gathers and transmits biometric input to child biometrics app 201, and then to a mobile app such as parent/child/therapist mobile app 202 which may also access behavioral health engagement platform 200 by the child patient, parent, or therapist. Gathered biometric input may include sleep cycles and other information, body temperature, breathing rate, heart rate, etc.

Also shown, parent/therapist web app 203 may be used by the parent or therapist to access the behavioral health engagement platform 200. Visible to certain users are certain front-end APIs/services 207 which include authentication and authorization services 208 which may, for example, authenticate parents as part of the process of gaining access to the platform after they have been invited by the therapist, or authenticate the child via biometric inputs. Authentication may involve verifying a personalized code or password or inputting pre-configured data at the parent user device for transmission from the parent GUI interface to the behavioral health engagement platform and data access services 214 of backend APIs/services 213. Also included in front-end APIs/services 207 are therapist modality analytics 209 which may be visible to the therapist and allow the therapist to select a diagnosis modality and content for display at the patient user display transmitted via the patient GUI interface. Content may include, for example, behavioral therapeutic exercise videos. Therapist modality analytics 209 may also compile and assess statistics on the child patient's behavioral therapy compliance and behavioral trends.

Front-end APIs/services 207 feed into backend APIs/services 213 which are not visible to users and provide access to, for example, data access services 214, for example, once a user is authenticated via authentication and authorization services 208. Database 215 of backend APIs/services 213 may serve as a database of content to be presented to the child patient for viewing at the patient user device via the patient GUI interface.

Also shown here are external integration services 204 which allow for the integration of external services such as electronic medical records platforms from external healthcare systems including the therapist's healthcare system via medical integration APIs 210. This allows for cross-provider opportunities between, for example, the therapist and other healthcare providers involved in the child patient's care. Through medical integration APIs 210, external healthcare providers may provide or get access to information about the child patient's behavioral health or general medical condition. For example, external electronic medical records may be able to inform the therapist's diagnosis by auto-populating or verifying the child patient's medical data into the behavioral health engagement platform for display at the parent/child/therapist mobile app 202 or parent/therapist web app 203. Other healthcare providers may also be receive alert notices or become otherwise informed of important changes or aspects of the child patient's behavioral health through medical integration APIs 210. According to certain embodiments, other healthcare providers may be those who would benefit from knowing about the child patient's behavioral health condition such as psychiatrists and pain management pediatricians.

Also shown is recommender engine 211 which may provide recommendations on content such as behavioral therapeutic exercise videos to be displayed at the parent/child/therapist mobile app 202 for the child patient to view. Recommender engine 211 may also, for example send other recommendations to the therapist such as best practices or standards of care regarding treatment for a certain diagnostic modality. According to certain embodiments, parents will also have on their parent-specific dashboard, links to articles related to each modality and technique to reference that will be stored and maintained by the behavioral health engagement platform 101. Moreover, therapists can add links for parent review on the basis of a particular patient, or based on a particular modality, or as a default setting, etc.

Finally, biometric analytics engine 212 may receive biometric data from child biometrics app 201 for analysis. Received biometric data may also be passed on to authentication and authorization services 208 to help authenticate the child patient and minimize the ability of other parties such as parents to manipulate data inputted by the child patient into parent/child/therapist/clinician mobile app 202.

In certain embodiments, biometric analytics engine 212 may have algorithms or other means of ascertaining gyroscopic information to eliminate confounders of anxiety or other behavioral health disorders such as exercise elevating heart rate.

Still further, in certain other embodiments, biometric analytics engine 212 may trigger alert notifications to be sent to the child when received biometric data is outside of a desired range, for example by sending an alert notification requesting the child to perform a behavioral health therapeutic exercise when biometric data indicates that heart rate is elevated.

In yet other embodiments, the biometric analytics engine 212 operates to implement novel analytical frameworks to complement operations facilitated by the behavioral health engagement platform 101, including, for example, executing instructions for performing (i) precision medicine operations, (ii) predictive analysis operations, and (iii) operations in support of "Tend and Befriend" psychological methodologies.

In support of such operations, the biometric analytics engine 212 may further interface with specially configured components of the behavioral health engagement platform 101 capable of executing such instructions on behalf of the platform, as follows:

A precision medicine function may be integrated with the biometric analytics engine 212 to execute instructions and perform operations which improve diagnosis and treatment outcomes personalizing mental health care by considering sociodemographic and clinical characteristics of each client such as age, comedication, organ functioning, comorbidities, symptoms, sleeping cycles, and patient preferences. In addition, the precision medicine function also operates to measure individualistic affinity to pharmacotherapies and non-pharmacotherapies to help patients mitigate risks where there is a lack of response, partial response or adverse reactions to treatment. Clinical care is significantly enhanced by incorporating objective monitoring of response to treatment and neurobiological data such as genetic biomarkers, neuropsychological evaluations, blood testing or brain imaging into the diagnostic process. For example, utilization of questionnaires aid the clinician with addressing health impacts of adverse childhood experiences (ACEs) as well as identifying how early life experiences in children impacts neurodevelopment facilitating targeted treatment by clinicians. The behavioral health engagement platform 101, in conjunction with the biometric analytics engine 212 and the precision medicine function further tracks and analyzes informative trends in epigenetics by implementing a systemic framework and methodology by which to understand how genetic expression may be modified by lifestyle factors by collecting data related to diet, obesity, physical activity, smoking, alcohol consumption, environmental pollutants, psychological stress, etc. Data collected from wearable devices via the behavioral health engagement platform 101 may further be consumed and analyzed by the precision medicine function to identify physiological markers for analysis at the point of impulsivity to determine effectiveness of treatment.

Similar to the precision medicine function, a predictive analysis function may be integrated with the biometric analytics engine 212 to execute instructions and perform operations which improve utilize statistics-based data analysis to make assumptions about the client application usage (e.g., use, interactions, and content consumption by a child patient) by capturing historical trends then applying the patterns of answers by the child patient to predict values for future sessions by keeping clinicians informed of favorable outcome data. Such predictive values rendered by the predictive analysis function may be applied to the same child patient, to a different child patient, or make up a data set which is utilized by the predictive analysis function to be applied to all child patients or child patients having a similar or overlapping class of characteristics or a similar cohort, etc. Such capabilities by the predictive analysis function thus allows clinicians to identify trends, test assumptions, and query patient data to interpret and forecast patient outcomes. The predictive analysis function may be further configured to utilize algorithms and an avatar to ask a series of questions, causing the behavioral health engagement platform 101 to issue GUI prompts to the display device of the child patient to screen for symptoms of mental health disorders as an adaptive system where questions are optimized and affirmations or encouraging words are offered based on the responses and emotional state of the child client.

Similar to the precision medicine and the predictive analysis functions described above, a "Tend and Befriend" function may likewise be integrated with the biometric analytics engine 212 to execute instructions and perform operations which implement a physiological and behavioral stress regulatory system that as an alternative to the flight and fight response for a child patient. The "tending" portion of such a function involves nurturing activities designed to protect family and friends, to promote a sense of safety, and to reduce distress, whereas the "befriending" portion is expressed in the creation and maintenance of social networks that facilitate the process.

Gamification methodologies may further be expressed by the behavioral health engagement platform 101 using the "Tend and Befriend" function which will not only help the child patient to visualize and remember tasks and goals but also actually implement new behaviors promoted by the "Tend and Befriend" function and the behavioral health engagement platform 101 generally as well as to overcome routines and bad habits. For instance, the "Tend and Befriend" function may be utilized in preference to a token economy gamification function as the "Tend and Befriend" function has been demonstrated to yield more effective outcomes in modifying trauma based behavior. Such outcomes are further enhanced when combined with the use of the precision medicine function and the predictive analysis functions described above, as it is critical to capture, review or analyze, and render predictive behavioral health interactions for a particular child patient based upon the particular psychological needs of that child patient, such as sensory simulation, role play, and meaningful activities or stories. In such a way, preferable to an extrinsic reward, such as a token, a system of activities using the "Tend and Befriend" function may be provided by the platform that correlate with intrinsic goals like being happier or more social even more successful will be created as a part of the onboarding process by the collective group of client, caregiver, and clinician and ultimately delivered to the child patient or to a group, class, or cohort of child patients by the behavioral health engagement platform 101. In certain embodiments, both gamification concepts may be applied, such that a combination of token rewards and a system of activities using the "Tend and Befriend" function may be provided to the child patient.

Figure 2B:
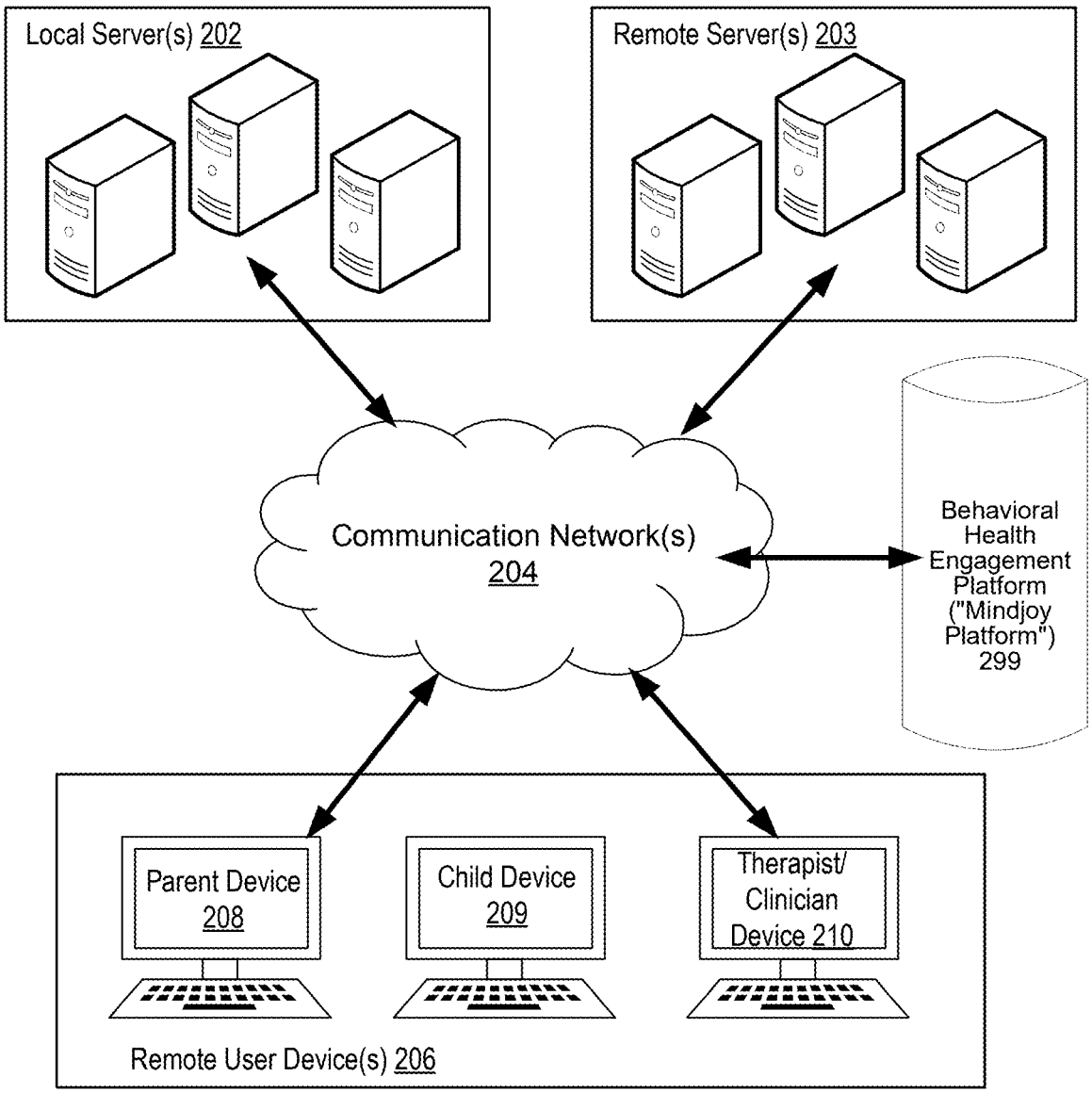
FIG. 2B depicts another exemplary computing architecture upon which the Integrative Behavioral Health Engagement Platform ("Mindjoy Platform") may operate, in accordance with described embodiments.

FIG. 2B depicts another exemplary computing architecture 201 upon which the Behavioral Health Engagement Platform ("Mindjoy Platform") 299 may operate, in accordance with described embodiments.

In particular, there is depicted here, both local servers 202 from which input data may automatically be retrieved and entered into the Behavioral Health Engagement Platform ("Mindjoy Platform") 299 or which may track localized data on behalf of the Behavioral Health Engagement Platform ("Mindjoy Platform") 299. For example, different certain data may be stored locally by a therapist's office for reasons such as data sensitivity, confidentiality, etc. Similarly, the therapist may create customized content and configuration information that may be stored locally, and thus, such data and content may be retrieved from the local repository at the local servers 202 and input into the Behavioral Health Engagement Platform ("Mindjoy Platform") 299.

Similarly, there are remote servers 203 depicted, which may take the form of cloud based remote storage or may take the form of remotely located client-server repositories. For example, the therapist may elect to upload customized content into the "cloud" in which chase, such consent is stored on the remote servers 203 and operable upon and retrievable by the Behavioral Health Engagement Platform ("Mindjoy Platform") 299, via the cloud based remote servers 203, as needed.

Similarly, machine learning models, training data sets for learning by machine learning models, configuration parameters, therapist specified settings, parent, child, and therapist account profiles and credentials, etc., may likewise be stored on the remote servers 203 within the "cloud," and thus be retrieved from the remote servers 203 and utilized to train, fine-tune, or to further enhance the predictive outcomes generated by the machine learning analytical models as well as support execution of specialized algorithm as applied via the Behavioral Health Engagement Platform ("Mindjoy Platform") 299, such as the selection mechanism of multi-media and interactive consent that is transmitted to a child patient based on the therapist diagnosis and based on each particular child's interactions with the Behavioral Health Engagement Platform ("Mindjoy Platform") 299.

Still further depicted are the various remote user devices 206 which communicate with the Behavioral Health Engagement Platform ("Mindjoy Platform") 299 and with the local and remote servers (202-203) via the communications network 204. For example, the depicted user devices 208-210 may be located at a child's home or school, a parent's home or work place, or a therapist's office. In particular, there are depicted the parent device 208 via which a parent may interact with a parent GUI and parent dashboard, a child device 209 via which a child may interact with a child GUI and interactive multi-media content transmitted to the child device 209, and a therapist device 210 via which a therapist may interact with a therapist GUI and therapist dashboard, for instance, to configure preferences and settings, to enter a diagnosis or modality for a child patient, or to configure and select multi-media content, or to electronically engage with and communicate with either the child or the child's parent.

Figure 3:
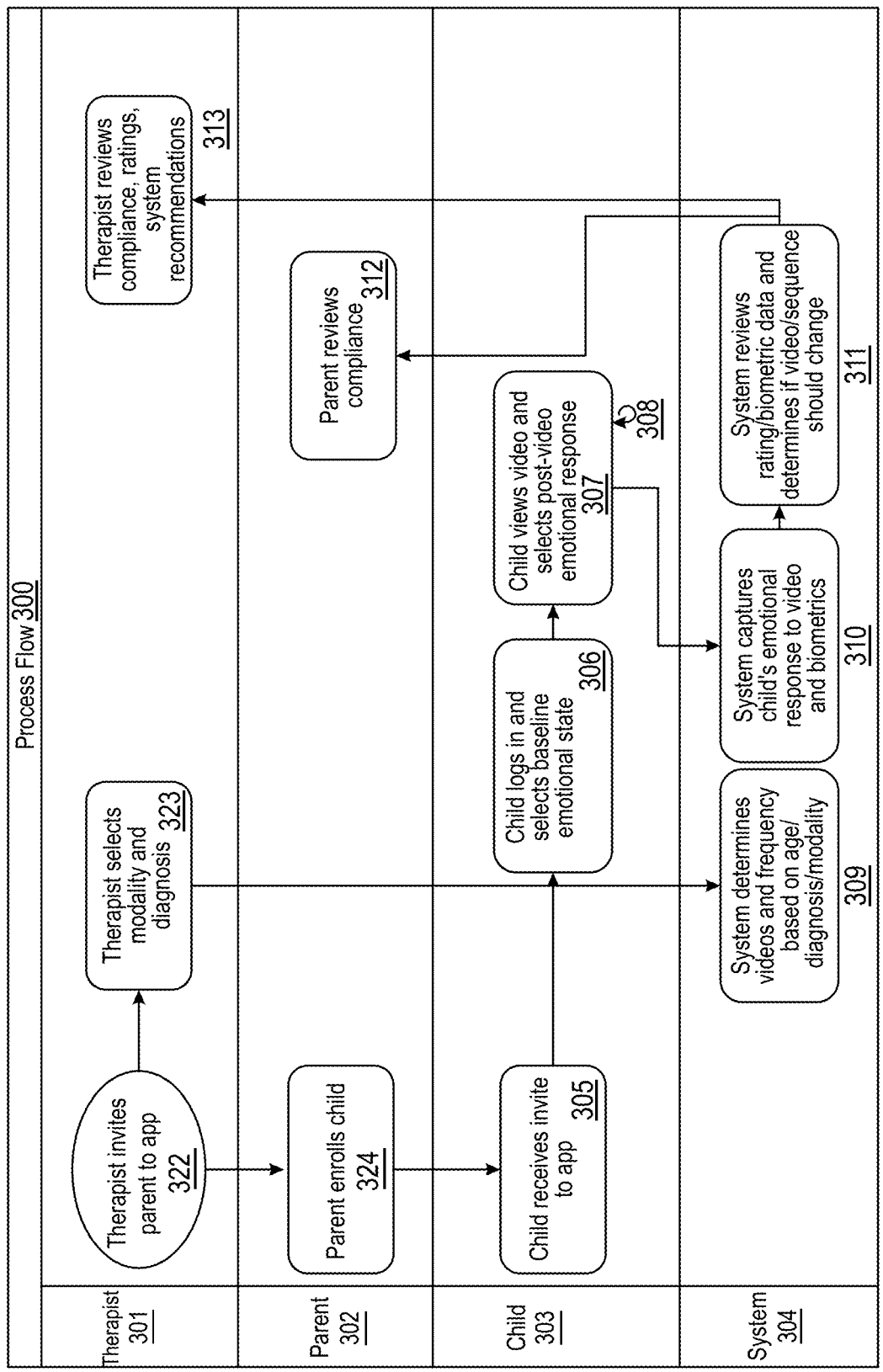
FIG. 3 depicts flow diagrams illustrating a method for implementing a behavioral health engagement and therapy outcomes tracking platform, in accordance with disclosed embodiments.

FIG. 3 depicts flow diagrams 300 illustrating a method for implementing a behavioral health engagement and therapy outcomes tracking platform, in accordance with disclosed embodiments.

Shown is process flow 300 which describes a process for using the behavioral health engagement platform. Actions in each row for therapist 301, parent 302, child 303, and system 304 show actions specific to each of these parties.

For example, the process flow 300 begins when a therapist invites a parent to the app 322. At this point, the therapist selects the modality and diagnosis 323 by selecting from pre-configured diagnosis and treatment modalities or creating such parameters. The system then determines videos and frequency based on age/diagnosis/modality 309. Videos presented to the child for viewing may also be pre-selected by the therapist based on these factors. According to other embodiments, health information specific to the child may be auto-populated into the app from external sources such as electronic medical records from the healthcare system in which the therapist practices or from the child's primary care provider's healthcare system. Following this, the parent enrolls the child 324. According to certain embodiments, this may involve the parent completing an intake questionnaire to provide demographic and health information about the child. The child then receives an invite to the app 305. According to some embodiments, this may involve an authentication process which verifies the child's identity by, for example, biometric input received via a biometric monitoring device and app, or alternatively voice or facial recognition software. At 306, the child selects his or her baseline emotional state by responding to questions that ask how they are feeling and why, including further questions about how strongly they are feeling a certain emotion and triggers for why they are feeling that way. The child then views a video and selects a post-video emotional response 307. According to some embodiments, the child's video viewing time may be captured, recorded, and stored so as to monitor compliance and to ensure that the child is not just briefly clicking on videos to quickly finish the session and earn rewards points.

After viewing the video, the child may be asked how they are feeling and if they would like to view another video 308. After the child views each video, the system captures the child's emotional response to video and biometrics 310. Biometrics may be captured through the biometric device attached to the child that is sending biometric data to the app. The child's emotional response is captured through questions asking about the child's emotional state, degree and triggers. Once data has been gathered from the child, the system reviews rating/biometric data and determines if video/sequence should change 311. Changed video and video sequences may be presented, for example, to the child at the next app session. Parents also have a chance to review compliance 312 and may see select information entered into the app by the therapist or child. According to certain embodiments, parents may enter information periodically, for example in the form of weekly questionnaires to updated the therapist on the child's condition. Finally, the therapist reviews compliance, ratings, and system recommendations 313 and may make his or her own adjustments to content or contact the child or parents.

Figure 4:
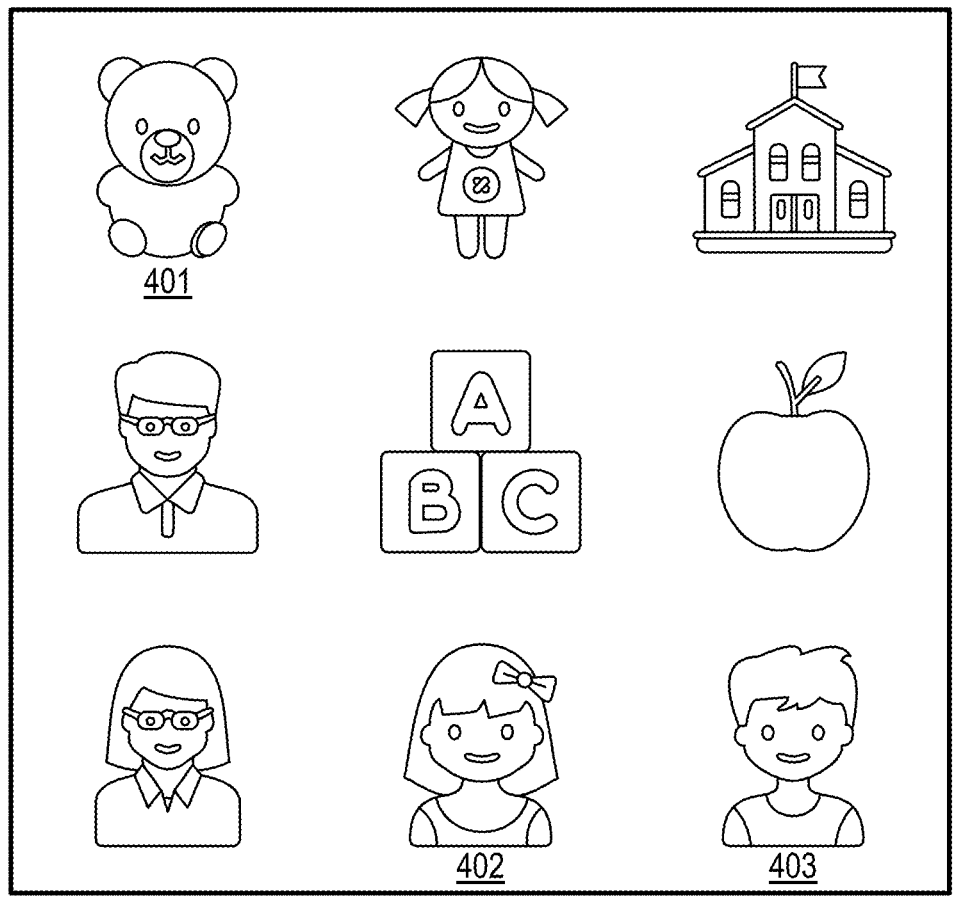
FIG. 4 depicts an exemplary avatar selection view, in accordance with described embodiments.

FIG. 4 depicts an exemplary avatar selection view 400, in accordance with described embodiments.

Shown here is exemplary avatar selection view 400 which the child may see according to some embodiments, during their first session on the behavioral health engagement platform. The child may select from various avatars such as bear 401, girl 402 or boy 403. The avatar will be associated with the child's account.

FIG. 5A depicts an exemplary emotional state selection view 500, in accordance with described embodiments.

As shown here, the child is greeted and asked about their baseline (current) emotional state 501. The child responds by selecting an emoticon from among emoticons representing various emotional states such as angry 505, sad 503 and happy 504, sick, mad, tired, pain, annoyed, worried, scared, lonely, etc.

Figure 5B:
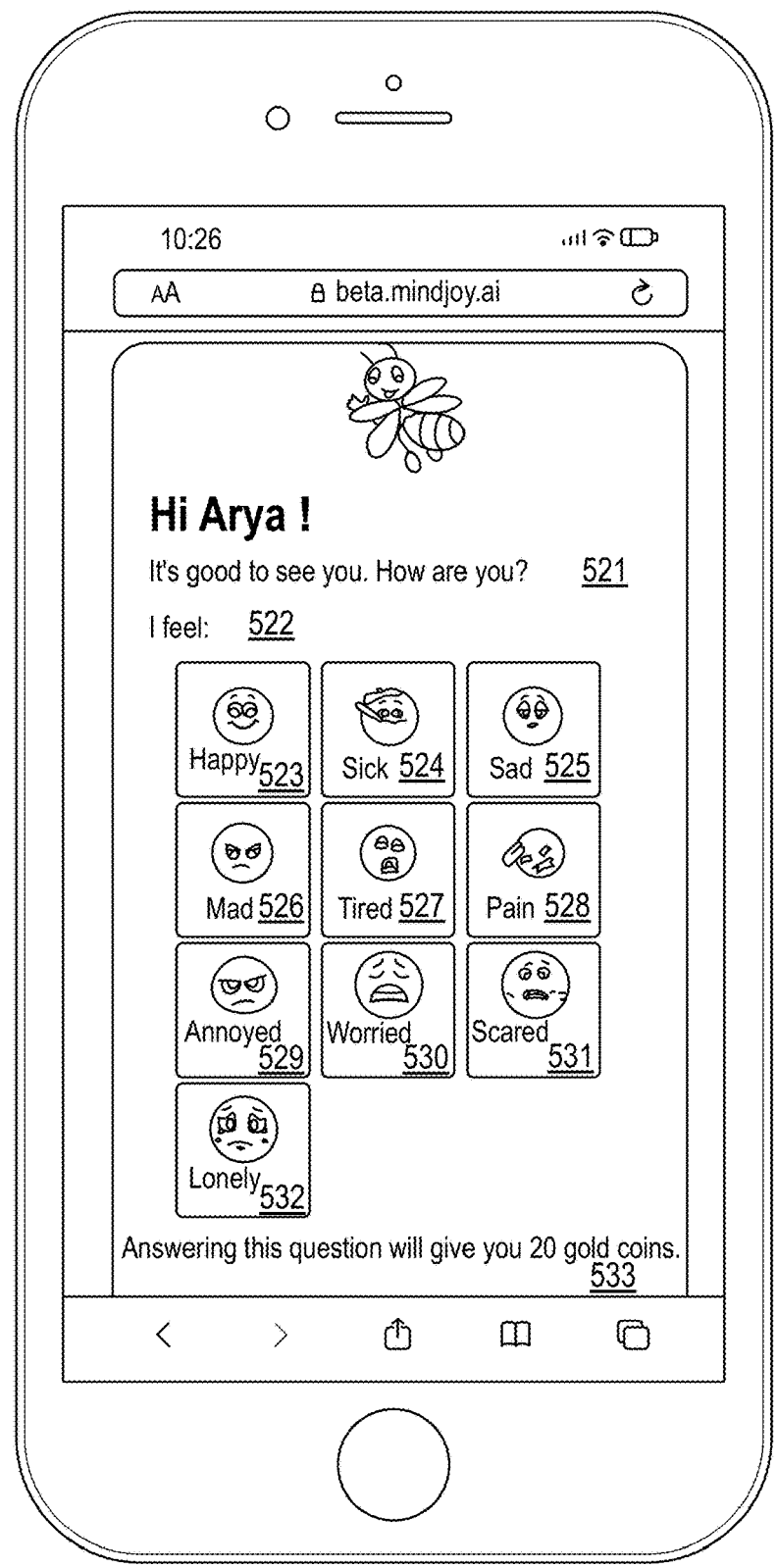
FIG. 5B depicts another exemplary emotional state selection view, in accordance with described embodiments.

FIG. 5B depicts another exemplary emotional state selection view 520, in accordance with described embodiments.

As depicted here, the selection view permits the child/patient to select their emotional state 523-532, responsive to the prompt 521. Additionally shown is the notification that "answering this question will give you 20 gold coins" 533, thus gamifying the system and incentivizing the child/patient to remain engaged with the behavioral health engagement platform 101.

Figure 5C:
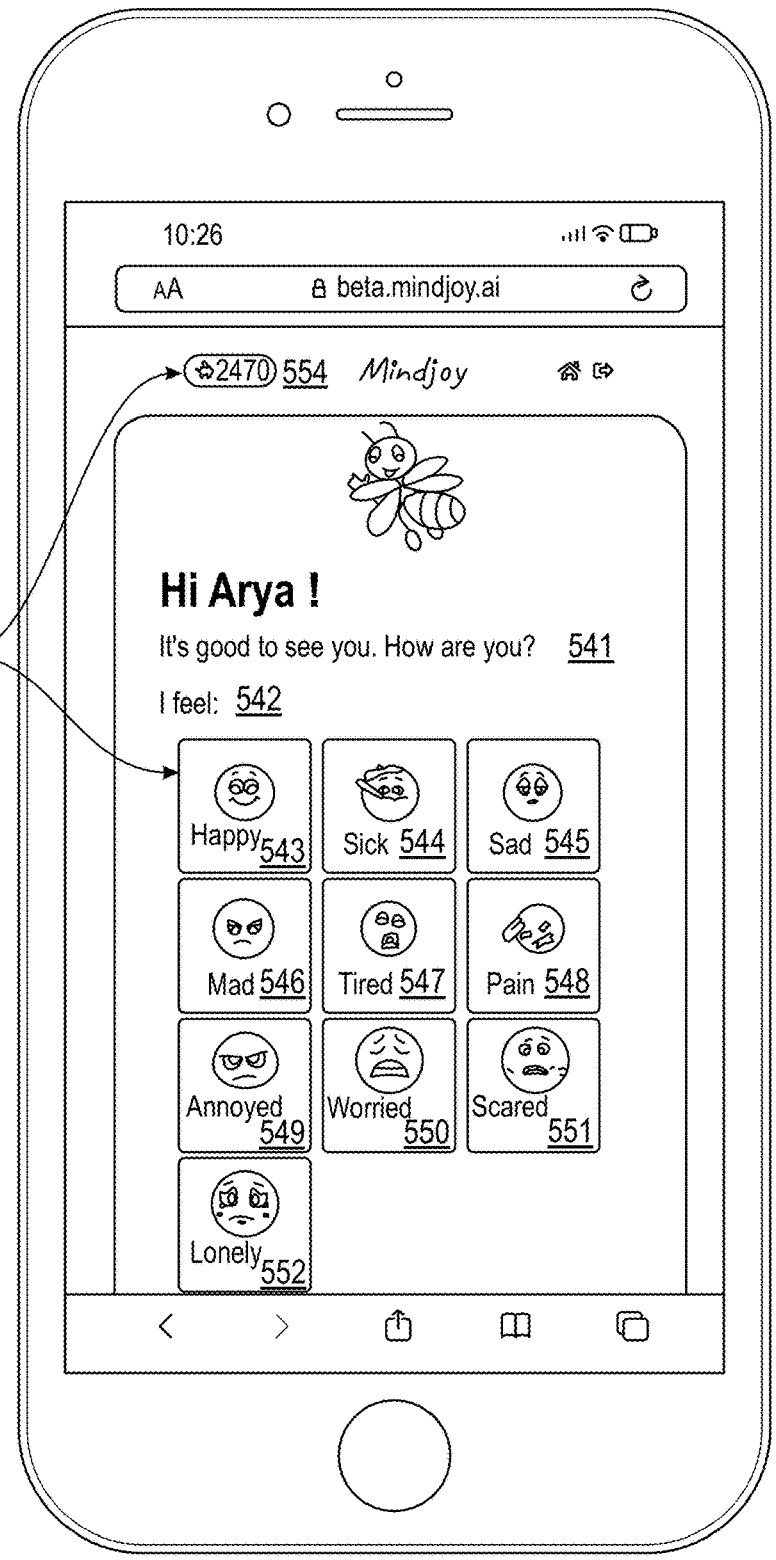
FIG. 5C depicts another exemplary emotional state selection view, in accordance with described embodiments.

FIG. 5C depicts another exemplary emotional state selection view 540, in accordance with described embodiments.

As depicted here, the selection view awards gold coins to the child upon making a selection 553 regarding a response to prompt 541 about the child's feelings 542 as represented by possible emotional states 543-552. As depicted, the child has accumulated 2470 gold coins 554.

Figure 6A:
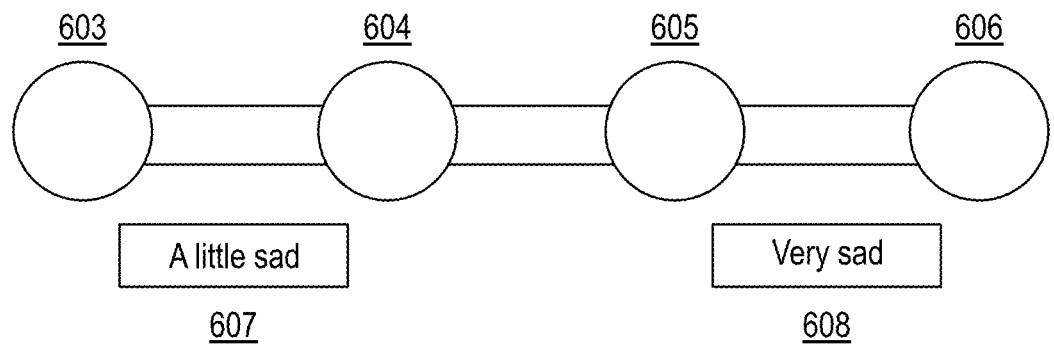
FIG. 6A depicts an exemplary sadness degree selection view, in accordance with described embodiments.

FIG. 6A depicts an exemplary sadness degree selection view 600, in accordance with described embodiments.

Following their selection of a baseline emotional state, the child rates the degree of emotion they feel. According to some embodiments, this may involve selecting a descriptor or number from a scale, drop down menu, etc. As shown here, the child who selected sad as their emotional state is asked how sad they are feeling 601. The child then selects by clicking on one of four points 603-606 on a sadness scale 602. Points 603 and 604 represent a little sad 607, while points 605 and 606 represent very sad 608.

Figure 6B:
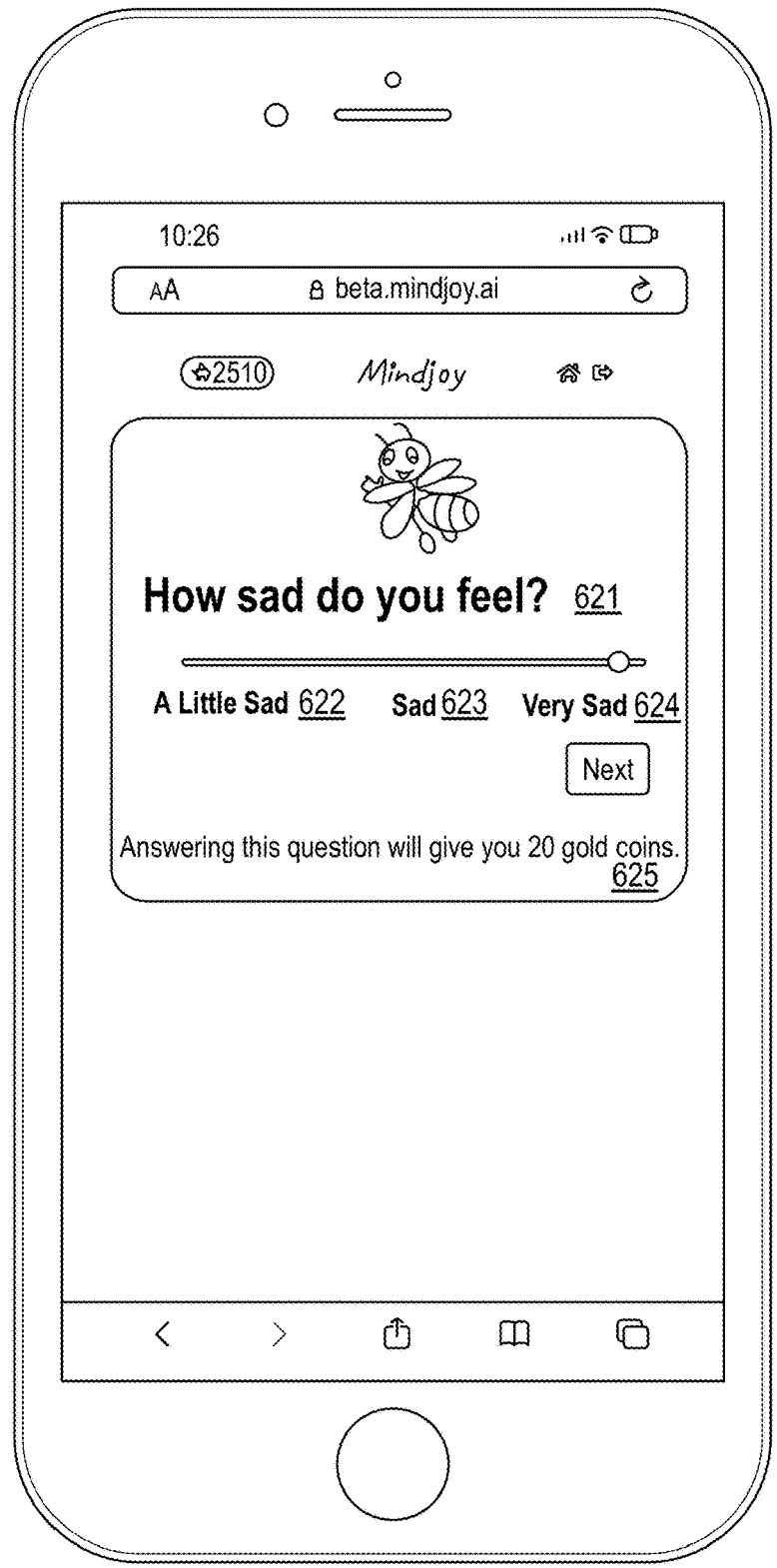
FIG. 6B depicts an alternative sadness degree selection view having only three points of selection instead of four, in accordance with described embodiments.

FIG. 6B depicts an alternative sadness degree selection view 620 having only three points of selection instead of four (a little sad 622, sad 623, and very sad 624), in accordance with described embodiments.

Figure 7A:
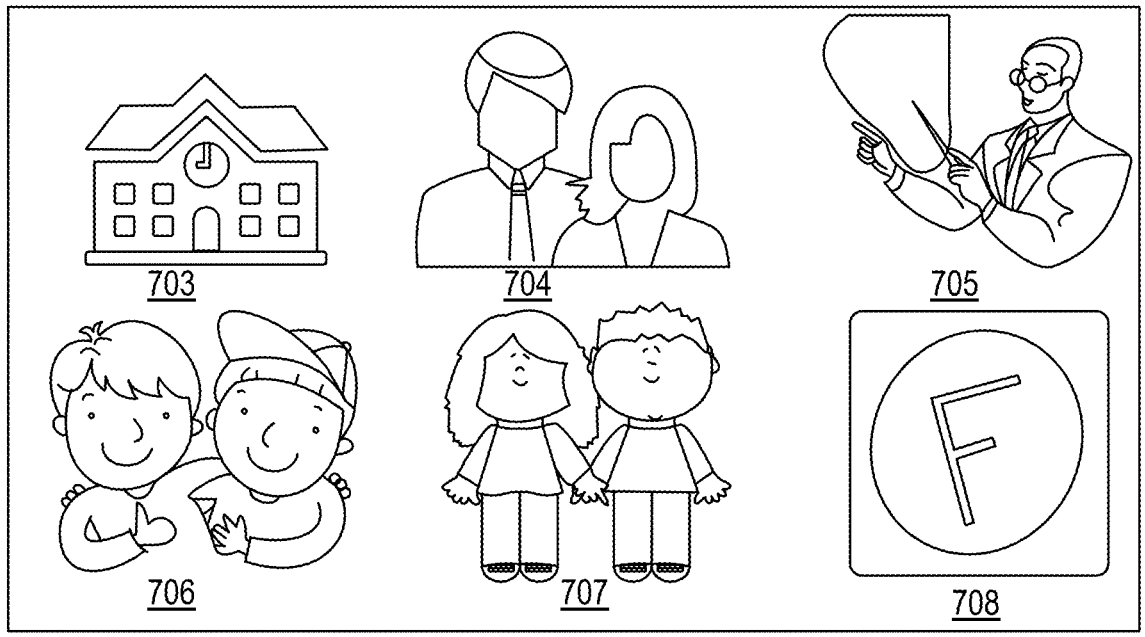
FIG. 7A depicts an exemplary emotional source trigger icon selection view, in accordance with described embodiments.

FIG. 7A depicts an exemplary emotional source trigger icon selection view 700, in accordance with described embodiments.

As shown here, the child is empathized with and asked why they are feeling a certain emotion (i.e. sadness) 701. The child may then select from various icons representing the source of their emotion (emotional trigger) 702 such as school 703, parents 704, a teacher 705, friends 706, siblings 707 or a bad grade 708. Many other examples exist. Moreover, the therapist may introduce customized selection options, such as social media, current events, another grownup, grandparents, etc. Alternatively, the therapist may select which subset from a larger list is to be presented to a particular patient or for a particular diagnosis, etc.

Figure 7B:
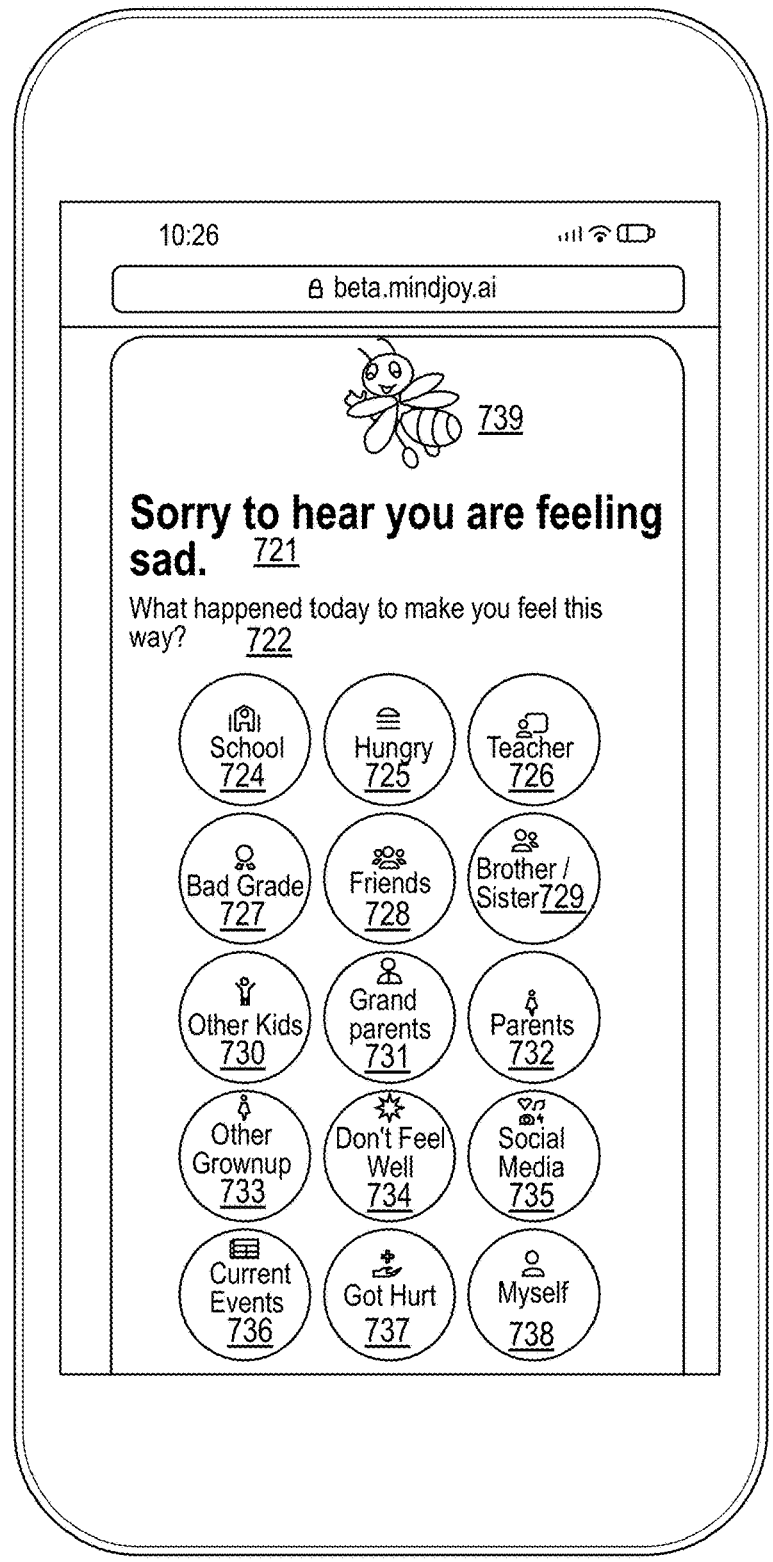
FIG. 7B depicts another exemplary emotional source trigger icon selection view, in accordance with described embodiments.

FIG. 7B depicts another exemplary emotional source trigger icon selection view 720, in accordance with described embodiments.

As shown here, the child is consoled 721 and prompted to make a selection corresponding to "what happened today . . . " 722 to make the child feel a particular way. Many selections are available, such as school 724, hungry 725, teacher 726, etc.

Additionally depicted here is the avatar 739 which is selectable by the child. The bee avatar 739 may be appropriate for young children, whereas the system may be configured to present different age-appropriate avatars to be selected for older children.

FIG. 8A depicts an exemplary emotional source trigger free-form text response view 800, in accordance with described embodiments.

As shown here, the child may be asked 801 about their emotional trigger but allowed more flexibility to enter text to describe their feelings in addition to or in the place of selecting from icons or a list. Free-form text box 802 allows for the child to input text to describe the source of their emotional trigger and providers more detailed information for review and analysis by the therapist and system.

Figure 8B:
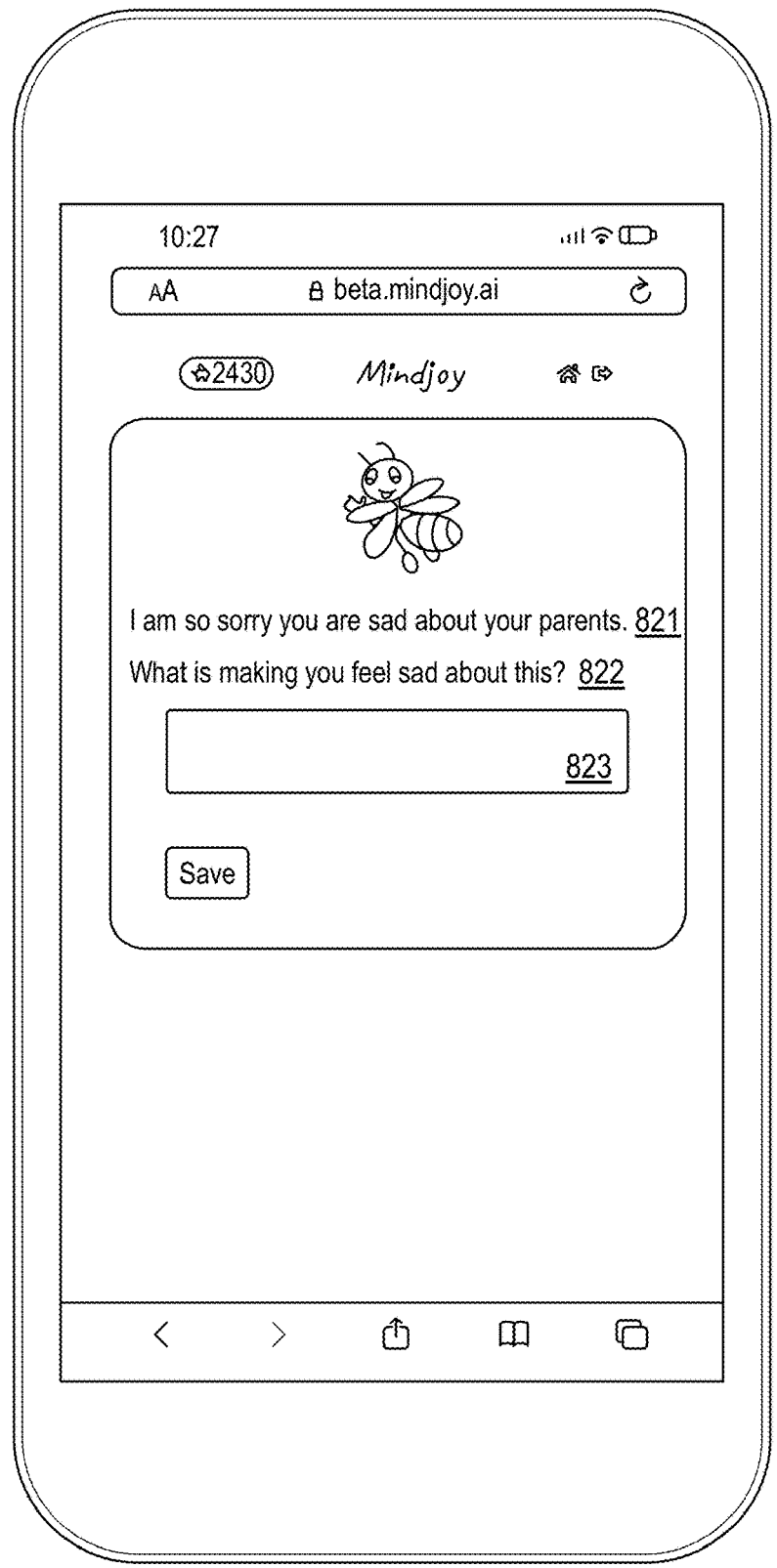
FIG. 8B depicts another exemplary emotional source trigger free-form text response view, in accordance with described embodiments.

FIG. 8B depicts another exemplary emotional source trigger free-form text response view 820, in accordance with described embodiments.

As before, the behavioral health engagement platform 101 prompts the child to describe what is making them feel sad 822, which may be entered into a free form text box or text area 823.

Figure 8C:
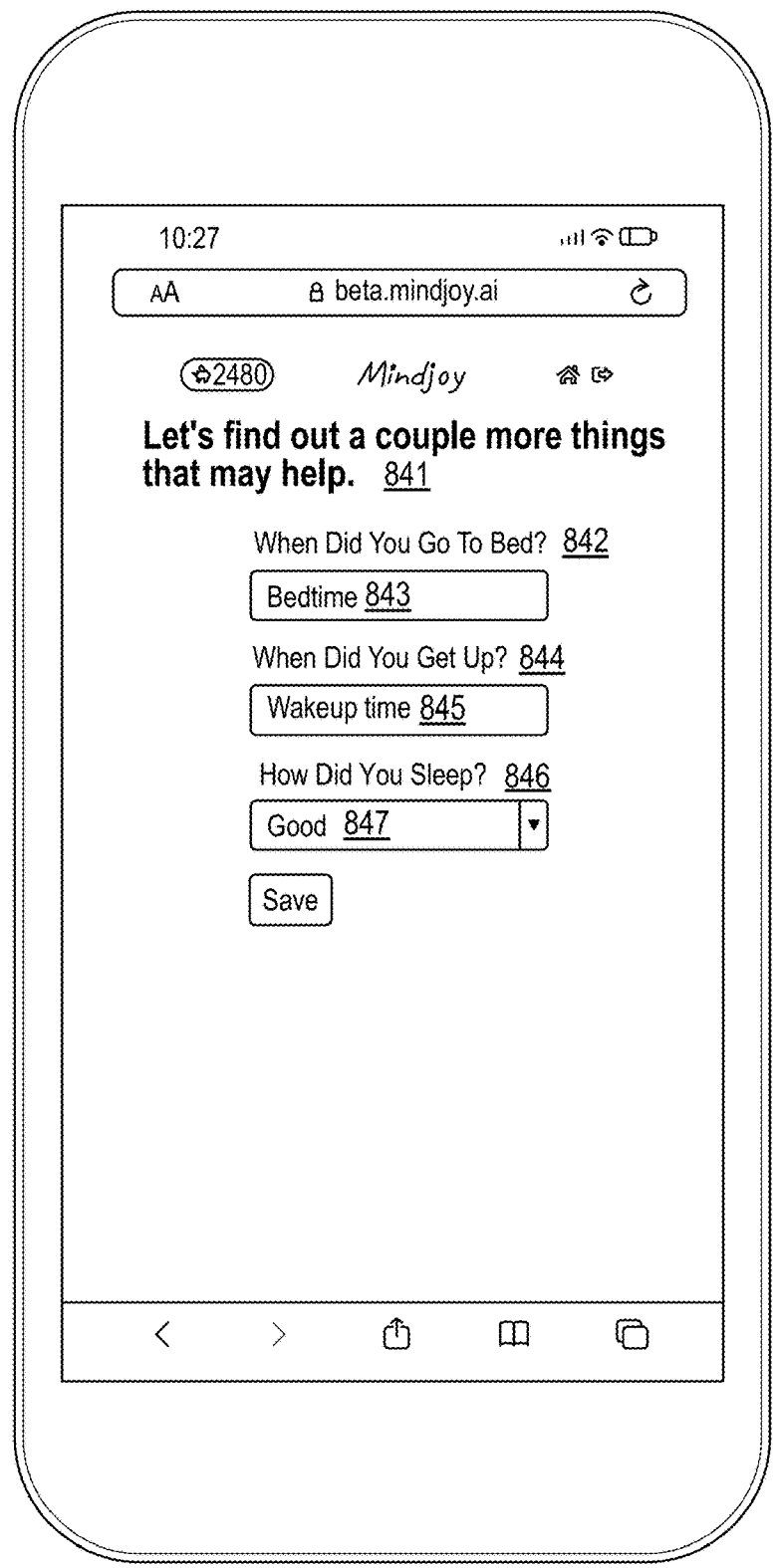
FIG. 8C depicts another exemplary emotional source response view, in accordance with described embodiments.

FIG. 8C depicts another exemplary emotional source response view 840, in accordance with described embodiments.

As shown here, the child is prompted to describe a few attributes or data-points 841 which may be helpful to the therapist in treating the child. For instance, the GUI interface depicted here requests the child to enter when they went to bed 842, his or her bedtime 843, when they woke up 844, and how they slept 846. For example, the child may report a good sleep 847 from a drop-down menu.

Such information may be utilized by the behavioral health engagement platform 101 to supplement biometric data collected or depending upon the configuration, such data may be utilized in place of biometric data collection.

Figure 8D:
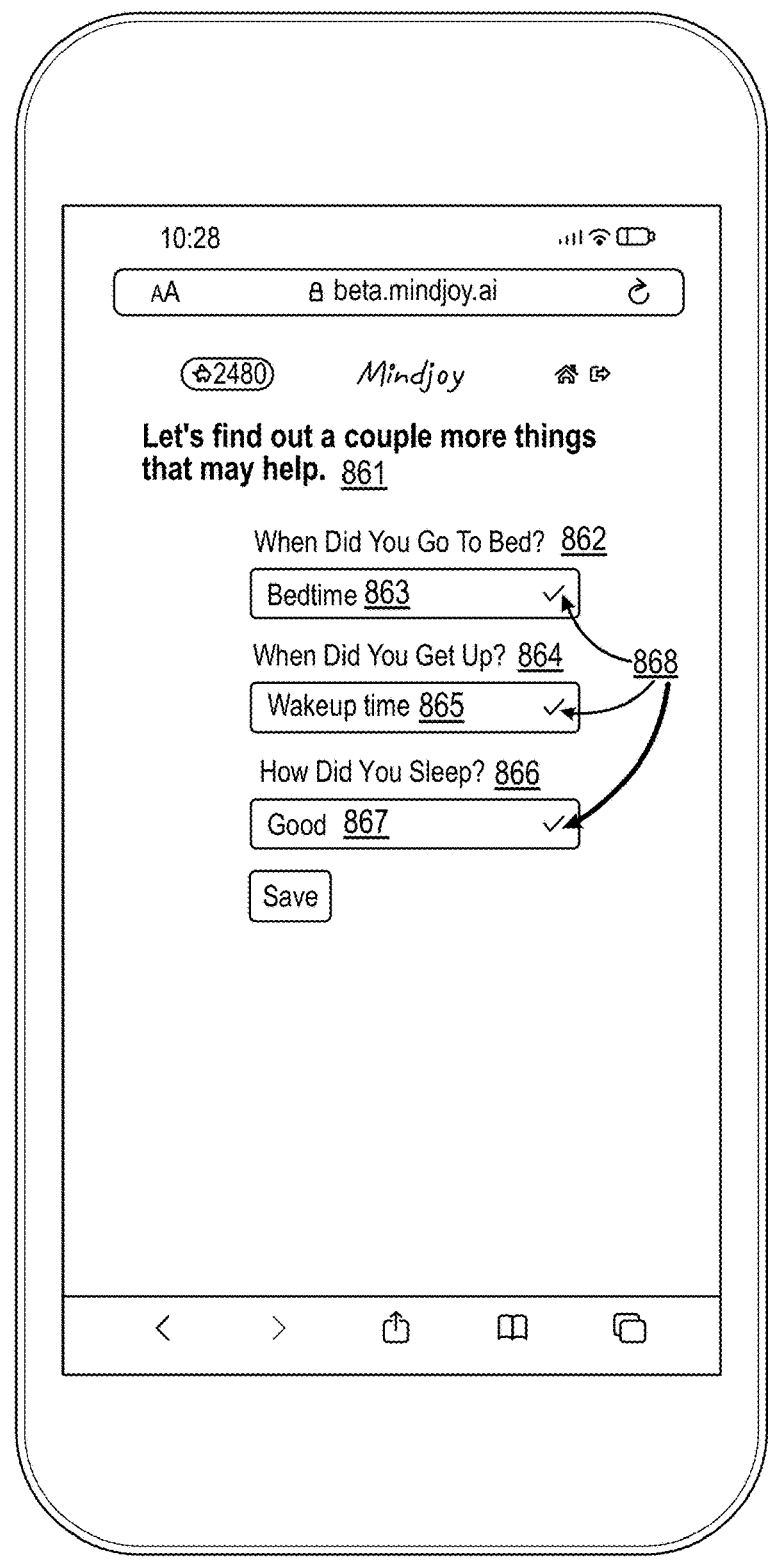
FIG. 8D depicts another exemplary emotional source response view, in accordance with described embodiments.

FIG. 8D depicts another exemplary emotional source response view 860, in accordance with described embodiments.

As shown here, the child has made selections 868 responsive to the prompts 862/864/866, which are then captured by the behavioral health engagement platform 101.

Figure 8E:
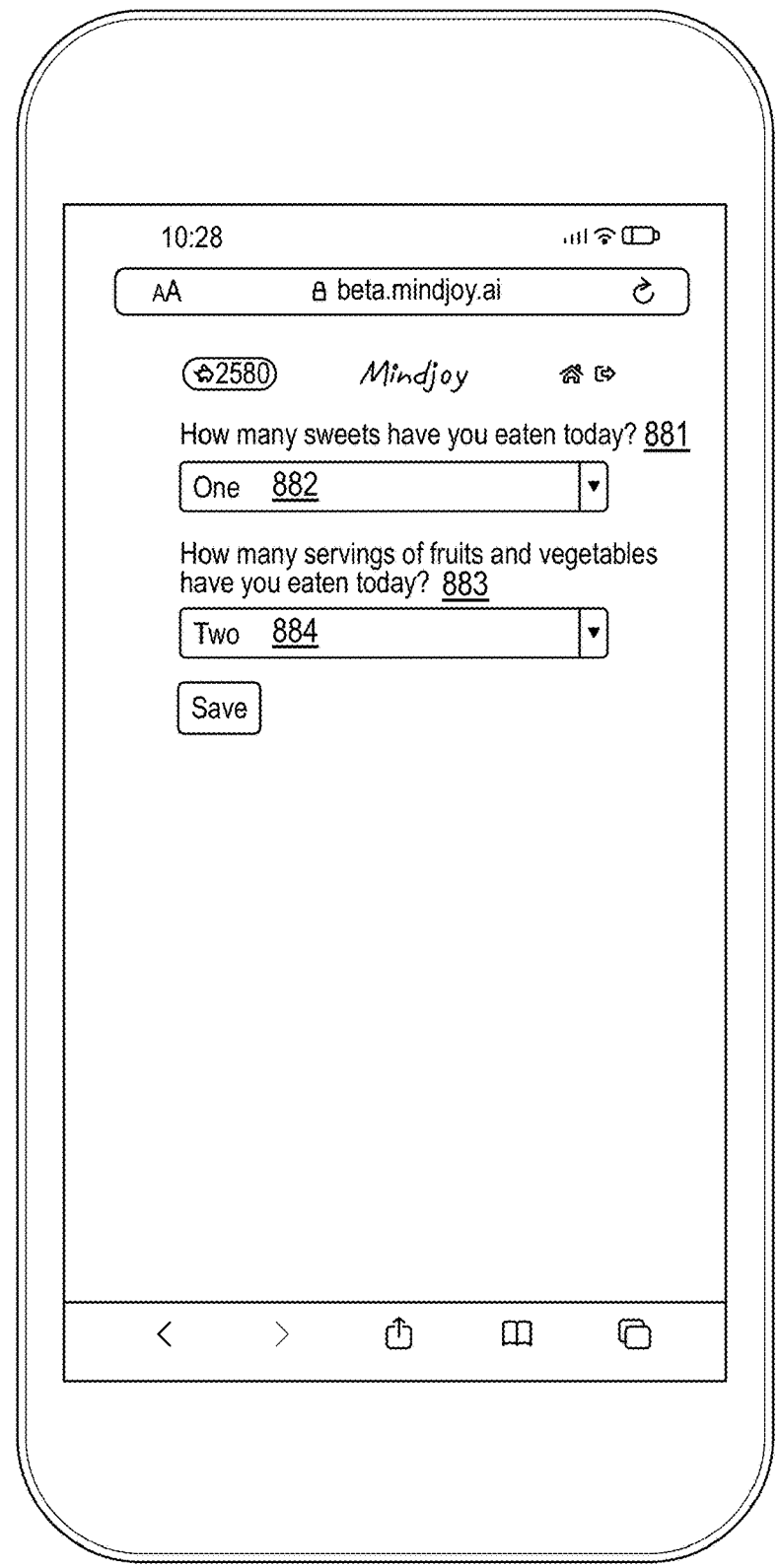
FIG. 8E depicts another exemplary emotional source response view, in accordance with described embodiments.

FIG. 8E depicts another exemplary emotional source response view 880, in accordance with described embodiments.

Similar to before, the child enters responses to prompts which are then utilized by the behavioral health engagement platform 101. Here the child answers 882/884 questions regarding how many sweets they consumed 881 as well as how many servings of fruits and vegetables were consumed 883.

Figure 9A:
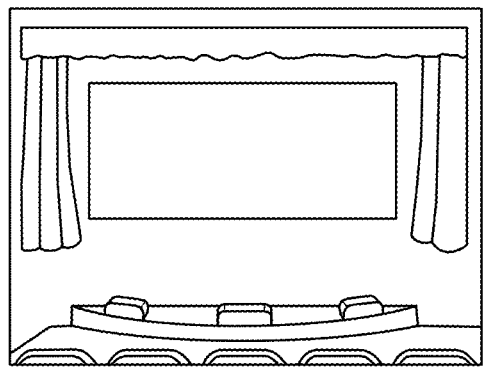
FIG. 9A depicts an exemplary behavioral therapy video presentation view, in accordance with described embodiments.

FIG. 9A depicts an exemplary behavioral therapy video presentation view 900, in accordance with described embodiments.

As shown here, once the child has identified and described their emotional state, they are presented with content for viewing in the form of a video 902 demonstrating a behavioral health therapeutic exercise which they are encouraged to follow along with 901. In certain embodiments, the video may be animated and be selected from a database or library of video content by the therapist or system. In other embodiments, the video may be live action and customizable, in which, by way of example, the therapist pre-records and appears in the video to build comfort and continuity of care with the child. The therapist may also receive notifications to update their video content over time.

Figure 9B:
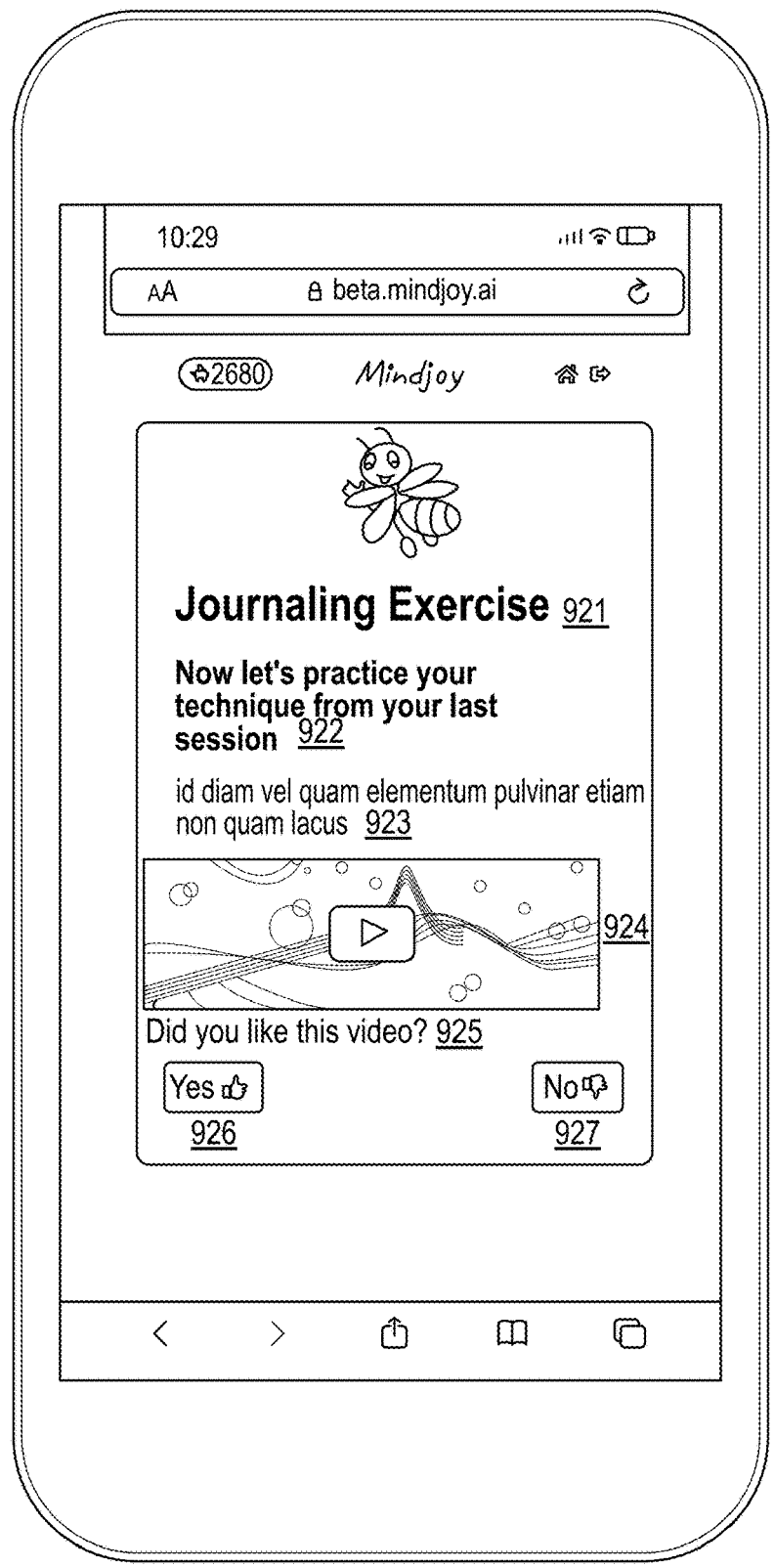
FIG. 9B depicts another exemplary behavioral therapy video presentation view, in accordance with described embodiments.

FIG. 9B depicts another exemplary behavioral therapy video presentation view 920, in accordance with described embodiments.

In this alternative view, there is notably the ability for the child to view a video selected by the system 924 (e.g. based on the therapist provided configuration and diagnosis) as well as the capture mechanism for whether the child liked the video 926 or did not like the video 927.

Additionally, here the behavioral health engagement platform 101 specifically configures the GUI interface and prompt 922 to reference the "journaling exercise" 921 that was discussed during the child's prior therapy session.

Figure 9C:
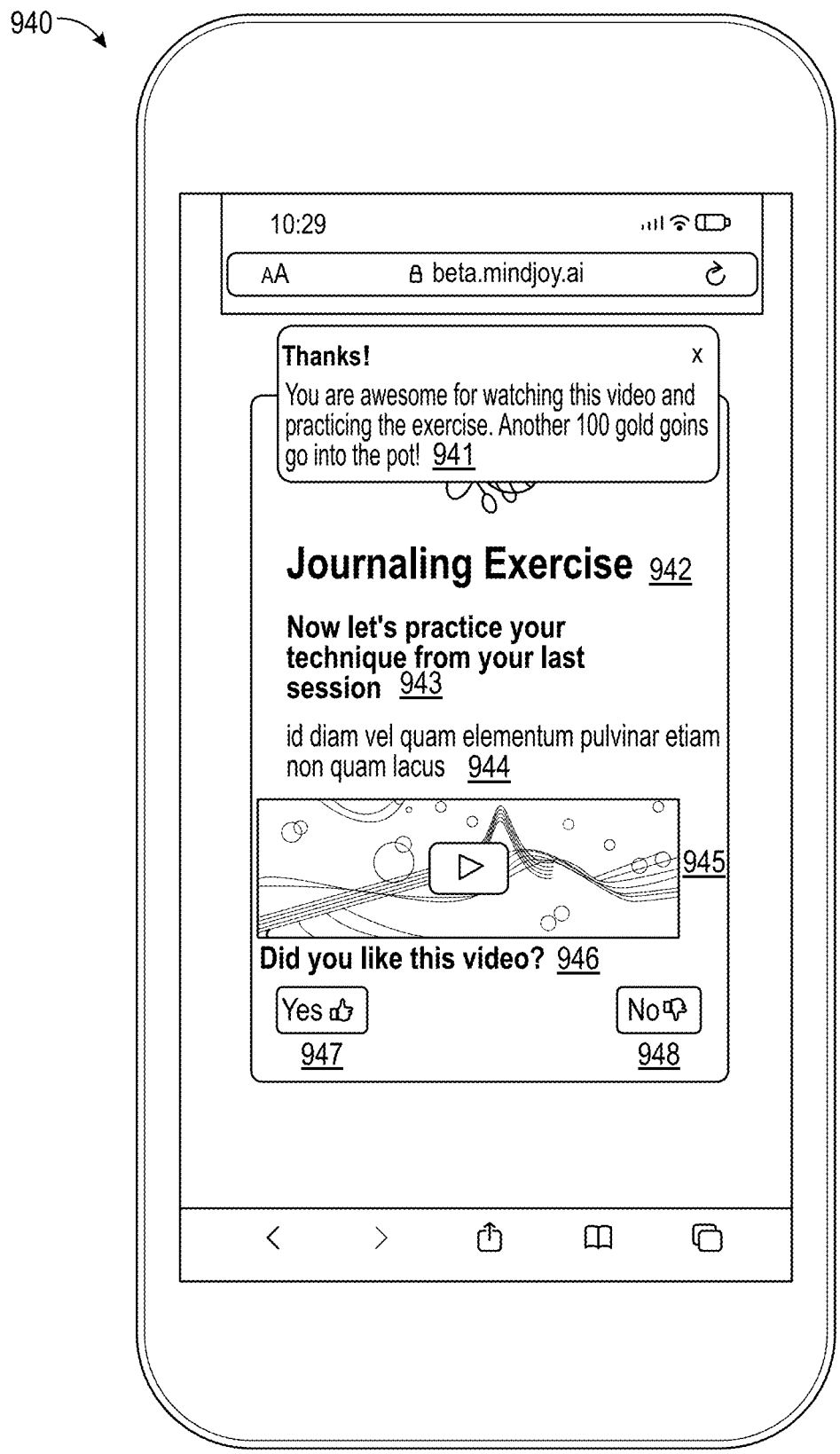
FIG. 9C depicts another exemplary behavioral therapy video presentation view, in accordance with described embodiments.

FIG. 9C depicts another exemplary behavioral therapy video presentation view 940, in accordance with described embodiments.

As shown here, the behavioral health engagement platform 101 thanks (e.g., via a prompt to the display device) the child for watching the video and allocates more gold coins to the child 941, thus further gamifying the interactions and encouraging child engagement.

FIG. 10 depicts an exemplary post-behavioral therapy video presentation binary rating view 1000, in accordance with described embodiments.

After viewing the video, the child is asked to rate the video 1001 by selecting from binary options yes 1002 and no 1003. According to other embodiments, the child may rate the video by entering text, selecting from a list of descriptors, etc.

Figure 11A:
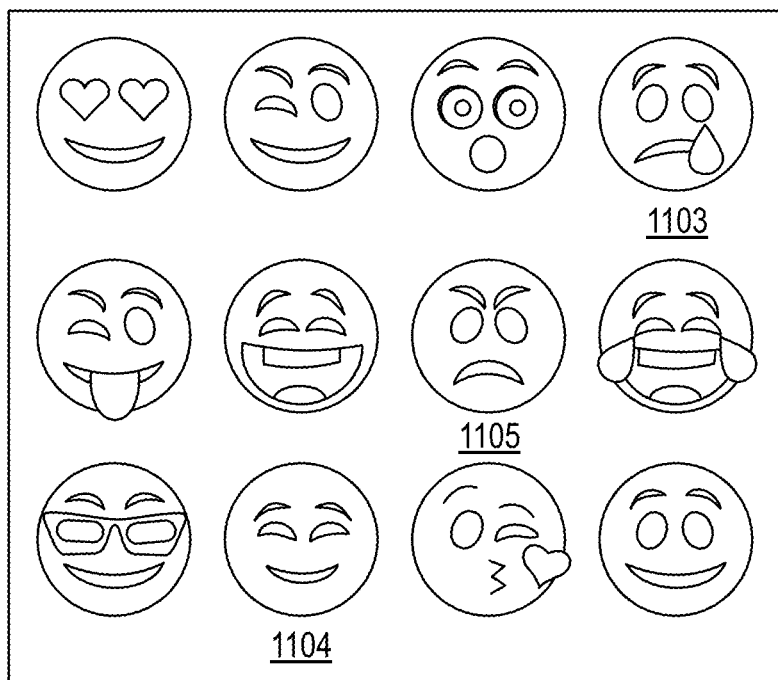
FIG. 11A depicts an exemplary post-behavioral therapy video presentation emotional state icon selection view, in accordance with described embodiments.

FIG. 11A depicts an exemplary post-behavioral therapy video presentation emotional state icon selection view 1100, in accordance with described embodiments.

In addition to rating the content such as videos, the child will also be asked how they are feeling now that they have viewed the content 1101. The child may select from a display of emoticons 1102 representing various emotional states 1103-1105 just as they did when they were asked about their baseline emotional state. Emoticons include angry 1105, sad 1103, and happy 1104.

Figure 11B:
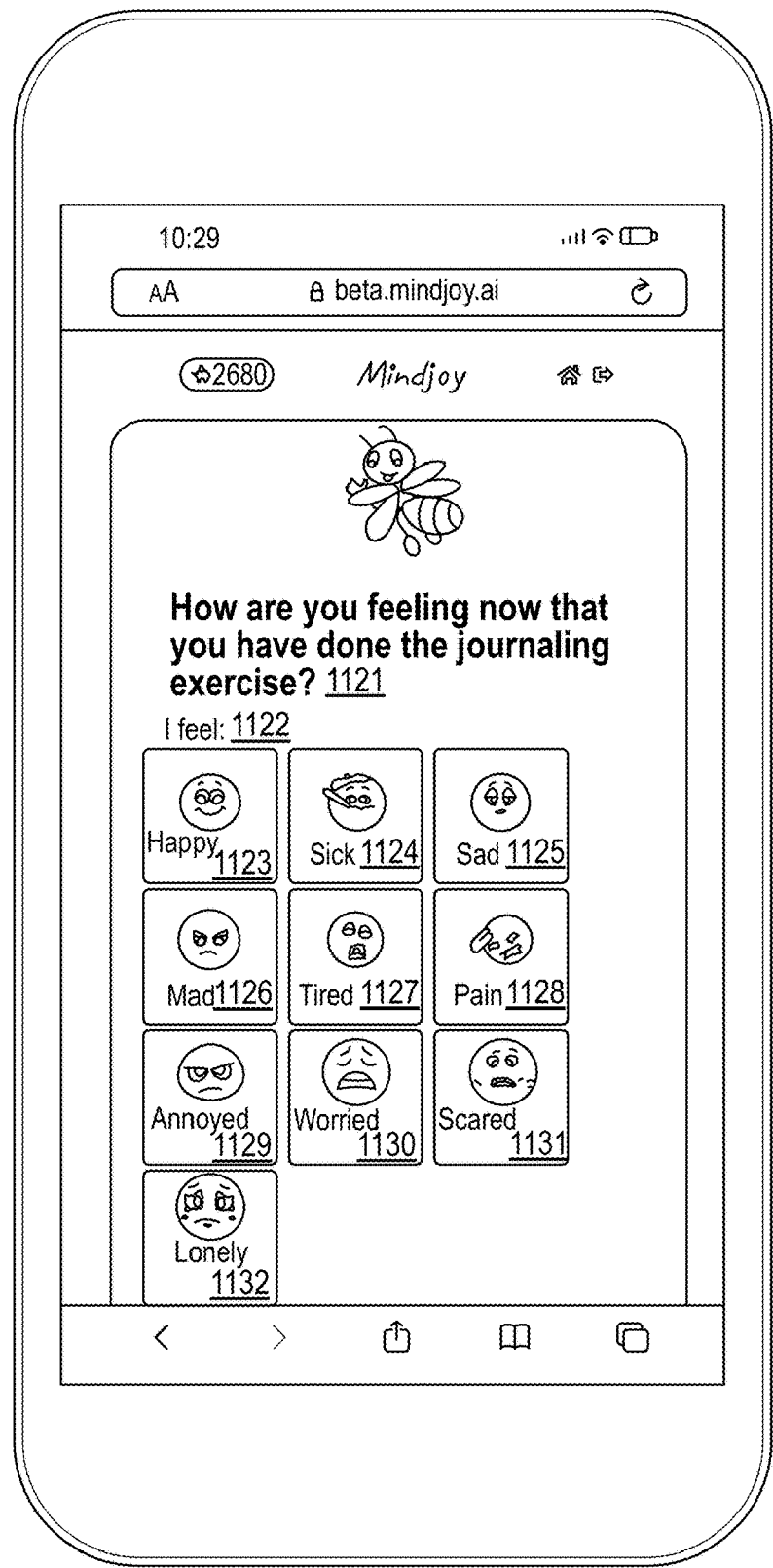
FIG. 11B depicts another exemplary post-behavioral therapy video presentation emotional state icon selection view, in accordance with described embodiments.

FIG. 11B depicts another exemplary post-behavioral therapy video presentation emotional state icon selection view 1120, in accordance with described embodiments.

As shown here, the behavioral health engagement platform 101 again prompts the child, now requesting them to identify how they are feeling subsequent to the previously referenced "journaling exercise" 1121. The child may specify 1122 that they feel happy 1123, sick 1124, sad 1125, mad 1126, tired 1127, pain 1128, annoyed 1129, worried 1130, scared 1131, and lonely 1132.

Figure 11C:
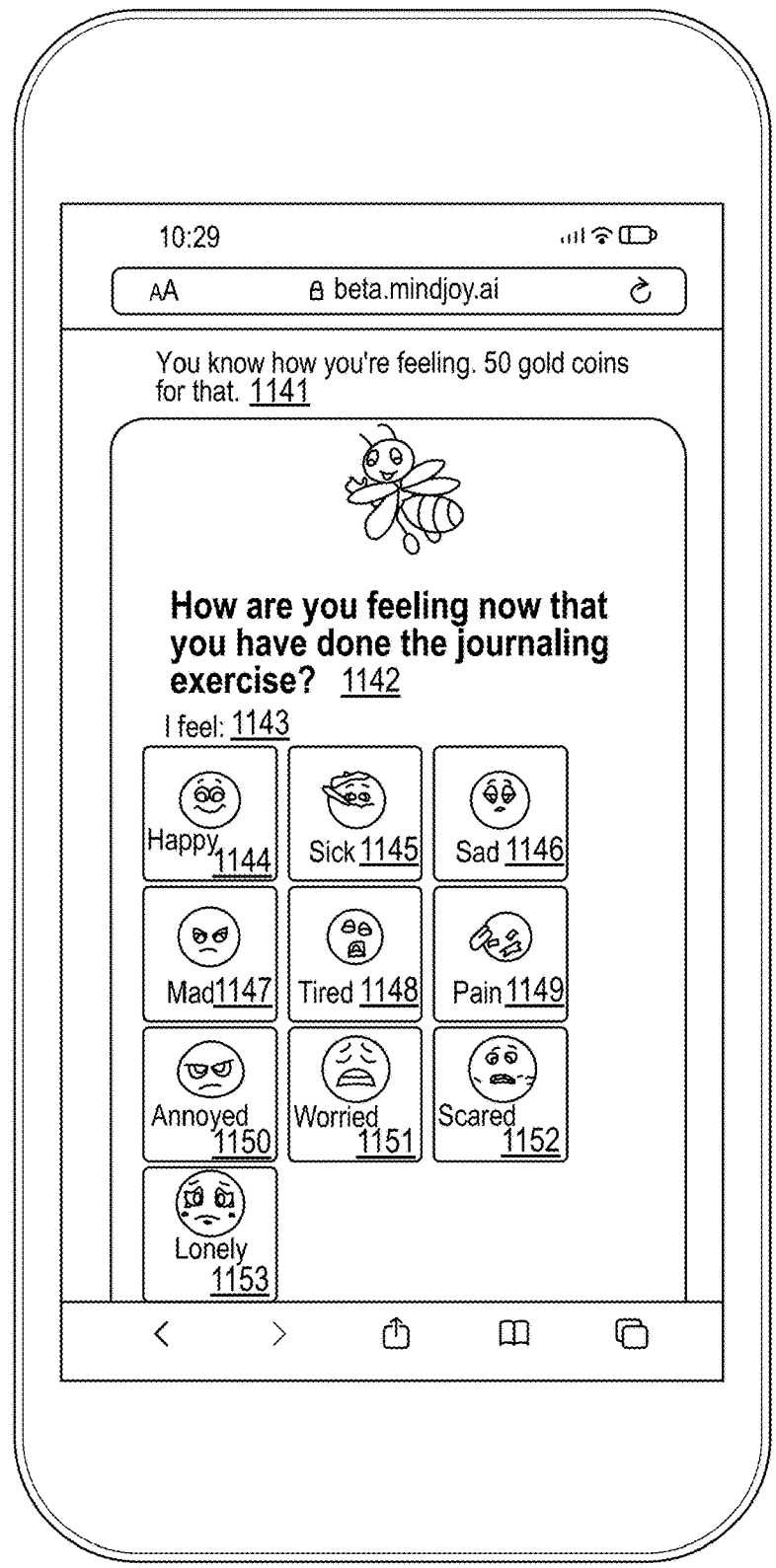
FIG. 11C depicts another exemplary post-behavioral therapy video presentation emotional state icon selection view, in accordance with described embodiments.

FIG. 11C depicts another exemplary post-behavioral therapy video presentation emotional state icon selection view 1140, in accordance with described embodiments.

As shown here, the behavioral health engagement platform 101 acknowledges the child's selection via the GUI and allocates more gold coins 1141.

Figure 11D:
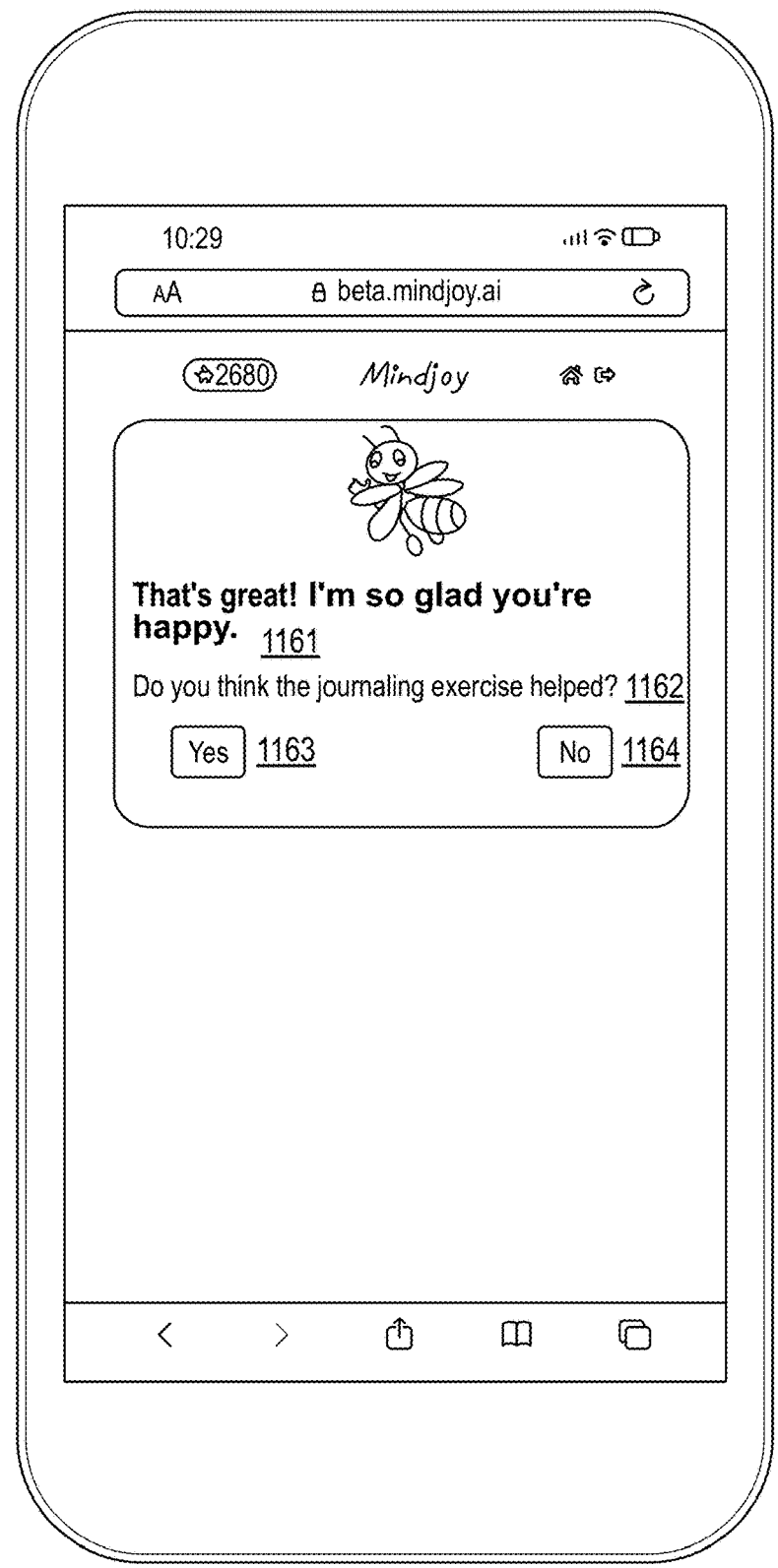
FIG. 11D depicts another exemplary post-behavioral therapy video presentation emotional state icon selection view, in accordance with described embodiments.

FIG. 11D depicts another exemplary post-behavioral therapy video presentation emotional state icon selection view 1160, in accordance with described embodiments.

As shown here, the behavioral health engagement platform 101 acknowledges the child's selection 1161 and solicits additional input from the child regarding whether or not the video content presented to the child was helpful 1162. The child may then select yes 1163 or no 1164 in response to the question 1162.

FIG. 11E depicts another exemplary post-behavioral therapy video presentation binary repeat selection view 1180, in accordance with described embodiments.

Here, the child is asked if they would like to watch another video 1181. This may be prompted by, for example, the child selecting an undesirable emotional state after watching the previous video. The child may select yes 1182 or no 1183.

FIG. 12A depicts an exemplary session completion and point total reporting view 1200, in accordance with described embodiments.

After completing content viewing, the child is ready to end the session. An exit message 1201 presents a notification pushed to the child GUI, thanking the child for their participation. According to some embodiments, a rewards summary message 1202 may inform the child the number of reward points they have accumulated during that session. According to other embodiments, the child may also be notified of the total points they have accumulated across all sessions. According to certain embodiments, reward points may be represented by coins or tokens. Rewards points may be awarded based on video content viewed and the child's responses including selecting emoticons, entering free-form text responses to questions, with each such task being worth a variable number of rewards points (for example 20-50 points). Rewards points may also be awarded for consistent use of the app. According to certain embodiments, rewards points may be redeemed with an online retailer or for a child-parent activity. According to yet other embodiments, the parent can configure or set reward redemption milestones, or follow default reward suggestions. A rewards points scheme may encourage the child's independent usage of and interaction with the behavioral health engagement platform.

According to certain embodiments, the child may also have the option to navigate from the session completion view back to previous data entered in order to correct or update his or her information.

According to the described embodiments, and further to that which is described above, the behavioral health engagement platform purposefully utilizes gamification of the application, so as to encourage continued engagement between the child/patient and the behavioral health engagement platform. For instance, the software will use digital game mechanical components to increase engagement, create intrinsic motivation to complete sessions, and promote learning by solving situational problems. These will include, but are not limited to points, in app currency, rewards, avatars, badges, timers, leader-boards, challenges, and storylines, etc. Such functionality is then paralleled with performance graphs or progress tracking metrics specific to the child/patient as they complete each technique per modality. With the advent of goals and objectives with instructions and regular interaction of answering questions about how to face challenging situations and make decisions, outcome data and feedback from a parent/therapist can encourage change in behavior.

Figure 12B:
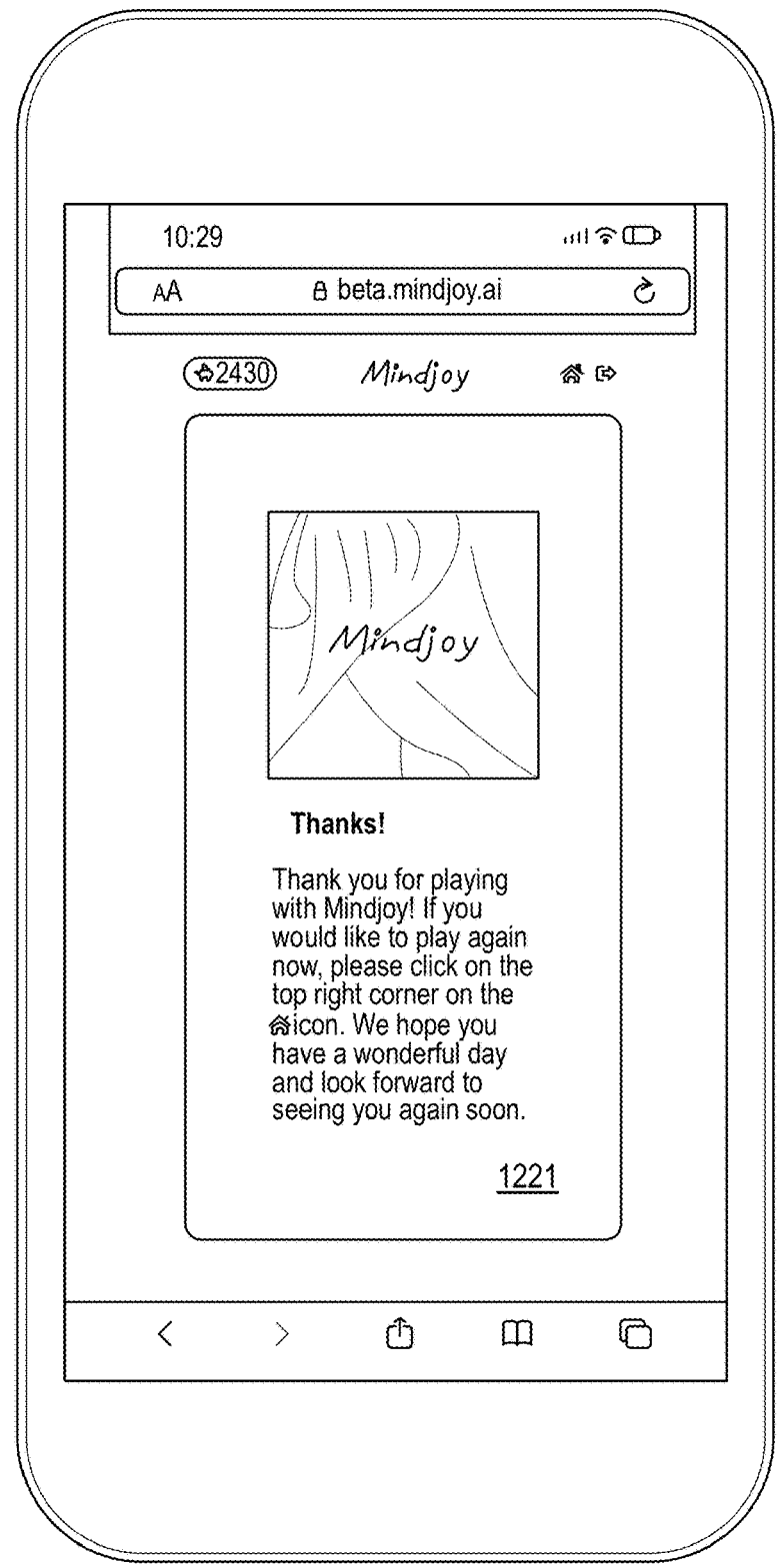
FIG. 12B depicts another exemplary session completion and point total reporting view, in accordance with described embodiments.

FIG. 12B depicts another exemplary session completion and point total reporting view 1220, in accordance with described embodiments.

As shown here, the behavioral health engagement platform 101 thanks the child for engaging with the platform and offers them the opportunity to play again 1221.

FIGS. 13A, 13B, 13C, 13D, 13E, 13F, 13G, and 13H depict various exemplary views of the therapist dashboard for use in conjunction with the behavioral health engagement platform 101, in accordance with described embodiments.

Figure 13A:
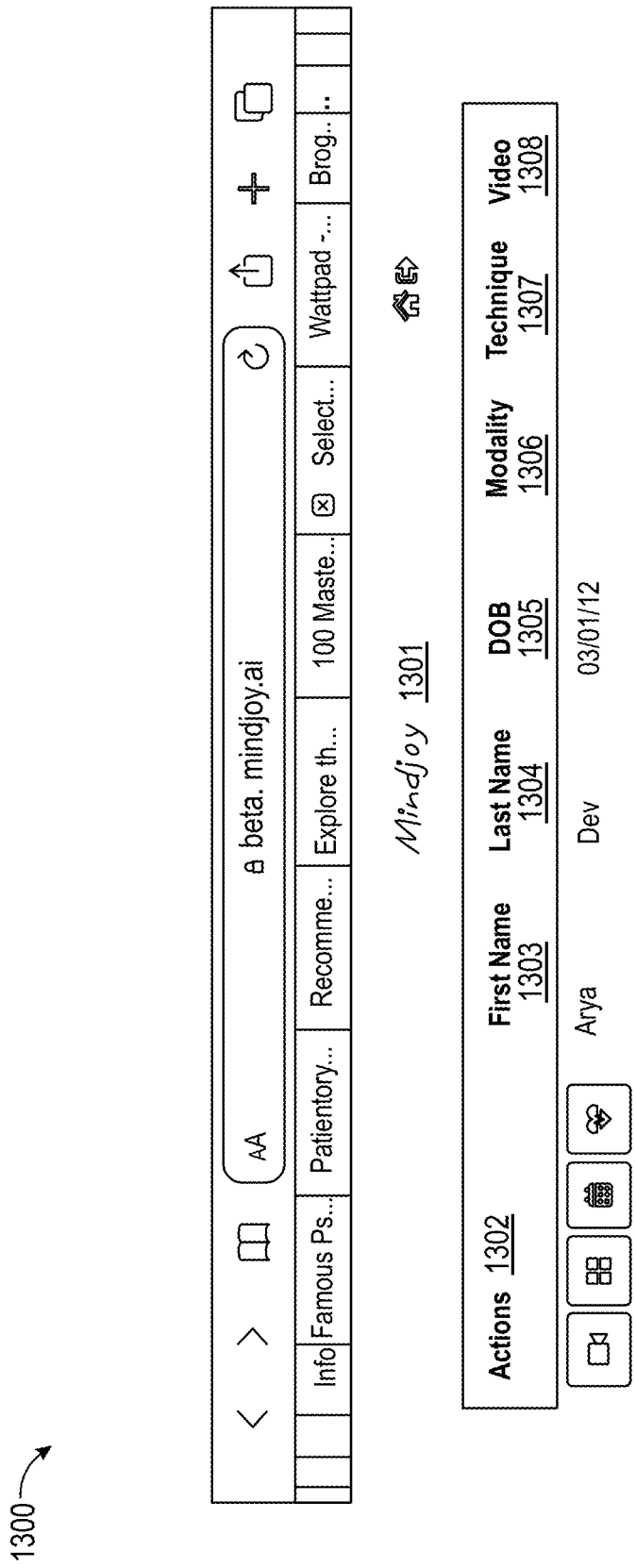
FIGS. 13A, 13B, 13C, 13D, 13E, 13F, 13G, and 13H depict various exemplary views of the therapist/clinician dashboard for use in conjunction with the behavioral health engagement platform, in accordance with described embodiments.

As shown at FIG. 13A, there is an exemplary therapist dashboard view 1300 depicting the listings and available actions 1302 for a particular patient or multiple patients. This may include patient information such as first name 1303, last name 1304, date of birth 1305. According to certain embodiments, information about treatment modality 1306, technique 1307, and videos 1308 may also display.

Figure 13B:
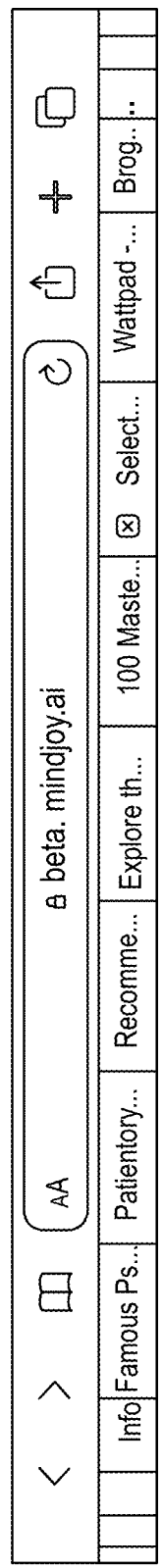
Figure 13C:
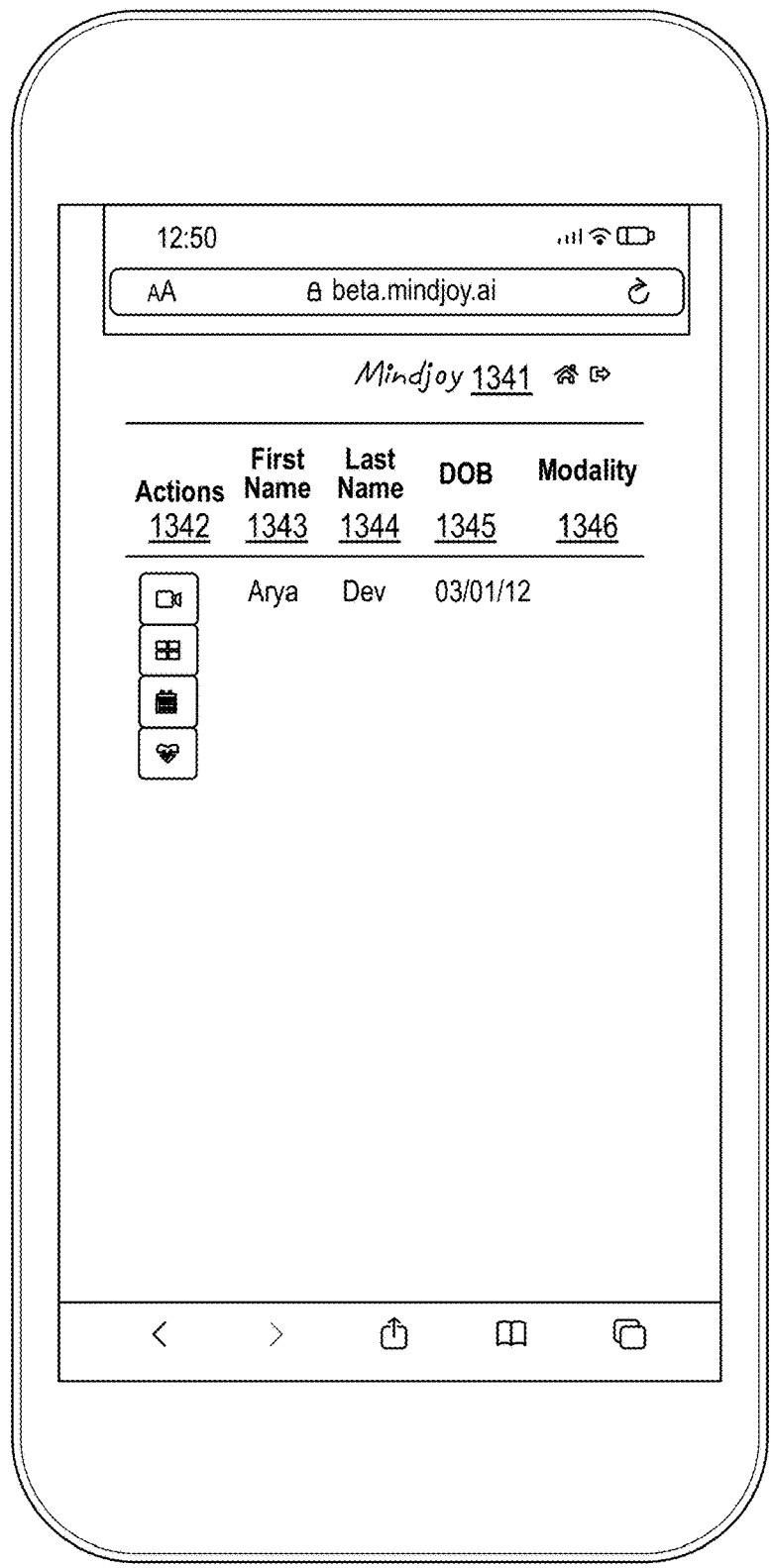

As shown at FIG. 13B, there is an exemplary therapist dashboard view 1320 in which the therapist may select and configure 1322 the determined modality for a given patient, for example, selecting CBT 1323, EMDR 1324, OCT 1325, etc.

Figure 13D:
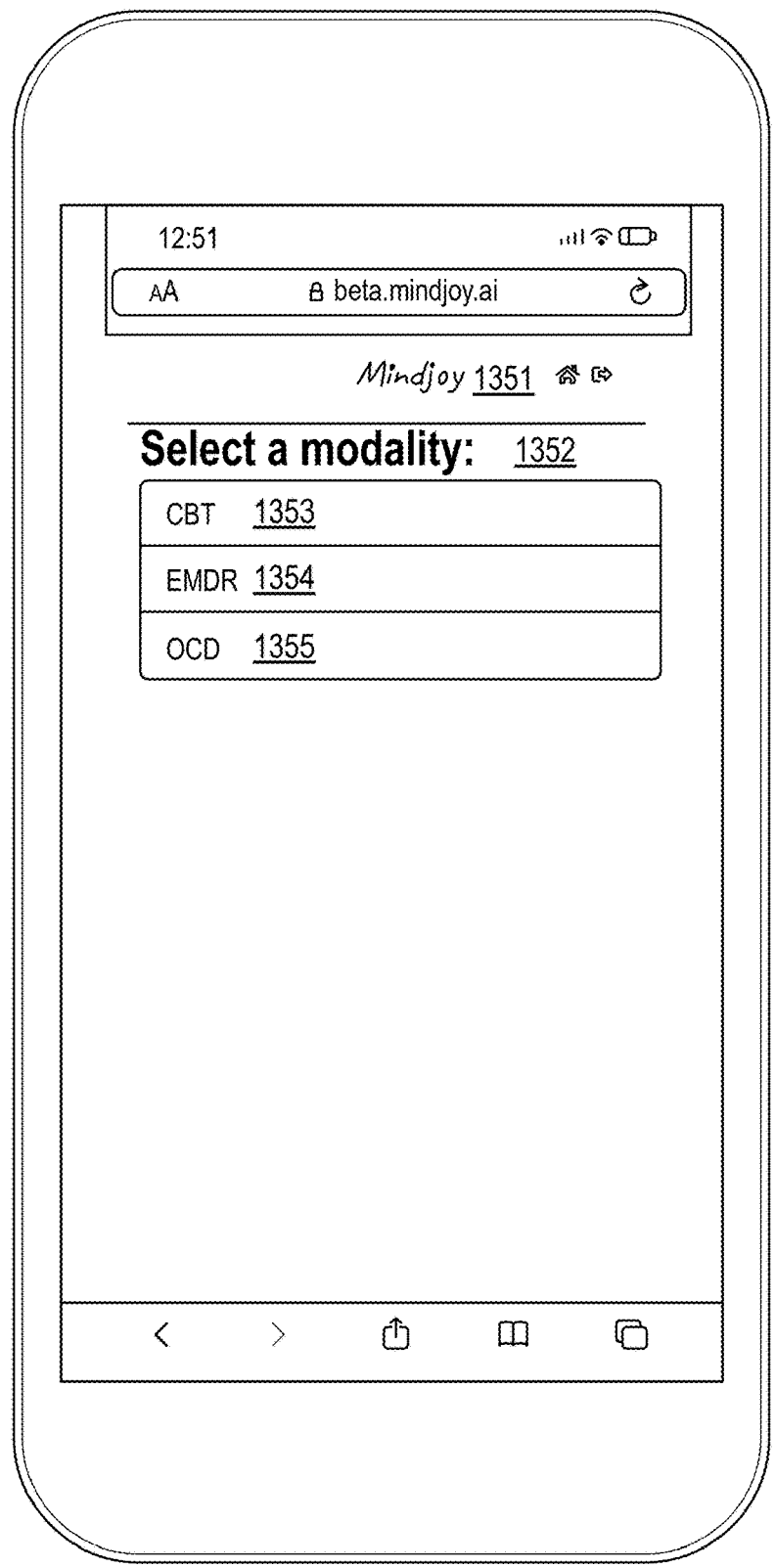

As shown at FIG. 13D, there is an exemplary therapist dashboard view 1350 in which the therapist may view various selectable actions configurable for a given patient based on modality as an alternative view to FIG. 13B.

Figure 13E:
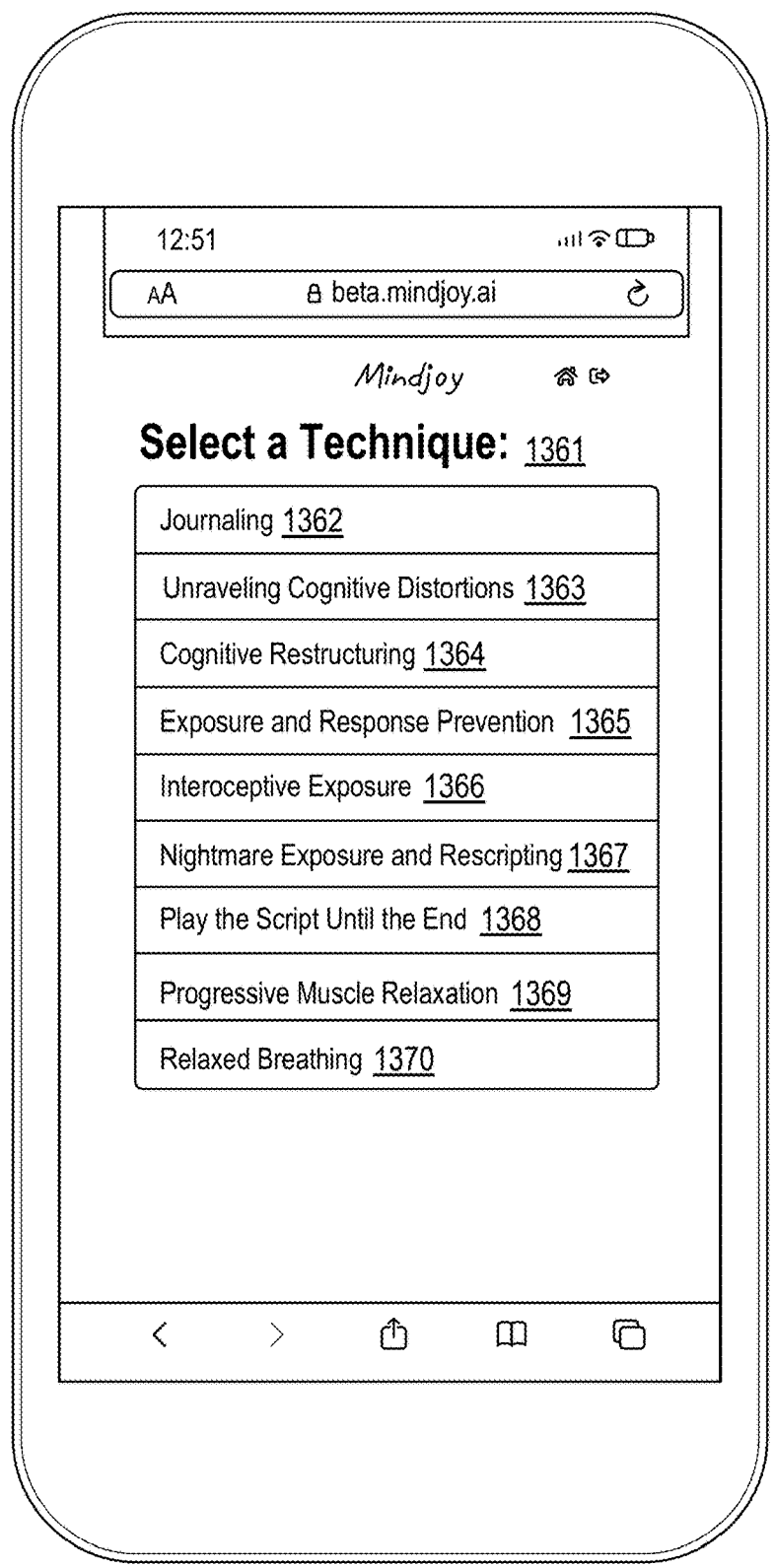

As shown at FIG. 13E, there is an exemplary therapist dashboard view 1360 in which the therapist may select and configure 1361 a variety of techniques 1362-1370 for the patient, such as journaling 1362, unraveling cognitive disorders 1363, cognitive restructuring 1364, exposure and response prevention 1365, interoceptive exposure 1366, nightmare exposure and rescripting 1367, playing the script until the end 1368, progressive muscle relaxation 1369, and relaxed breathing 1370.

Figure 13F:
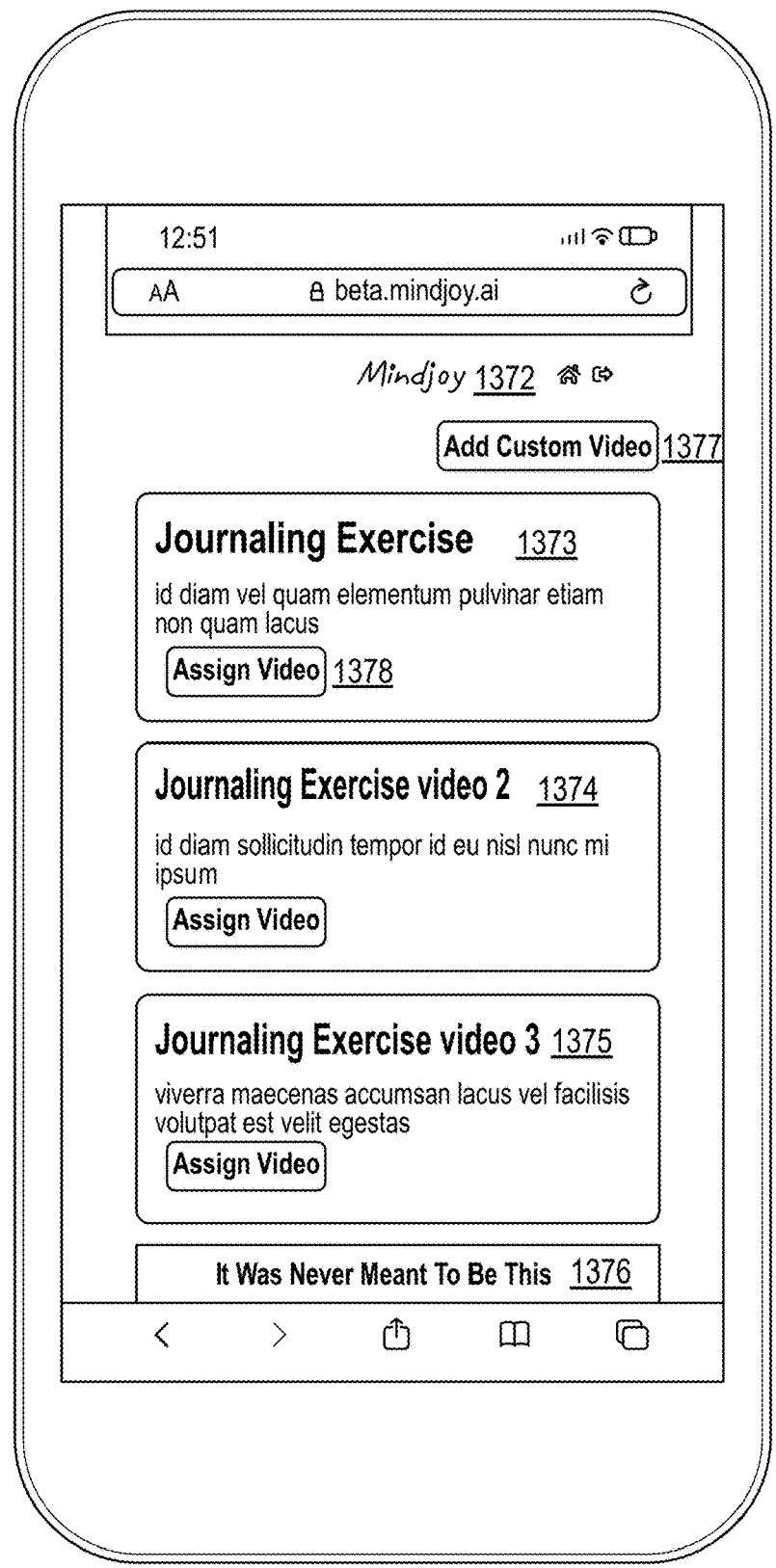

As shown at FIG. 13F, there is an exemplary therapist dashboard view 1371 in which the therapist may select and configure additional details and options for the selected techniques configured at the prior view 1360 for the patient. For example, the therapist may add 1377 or assign 1378 a video for the journaling exercise technique 1373 which was previously selected.

Figure 13G:
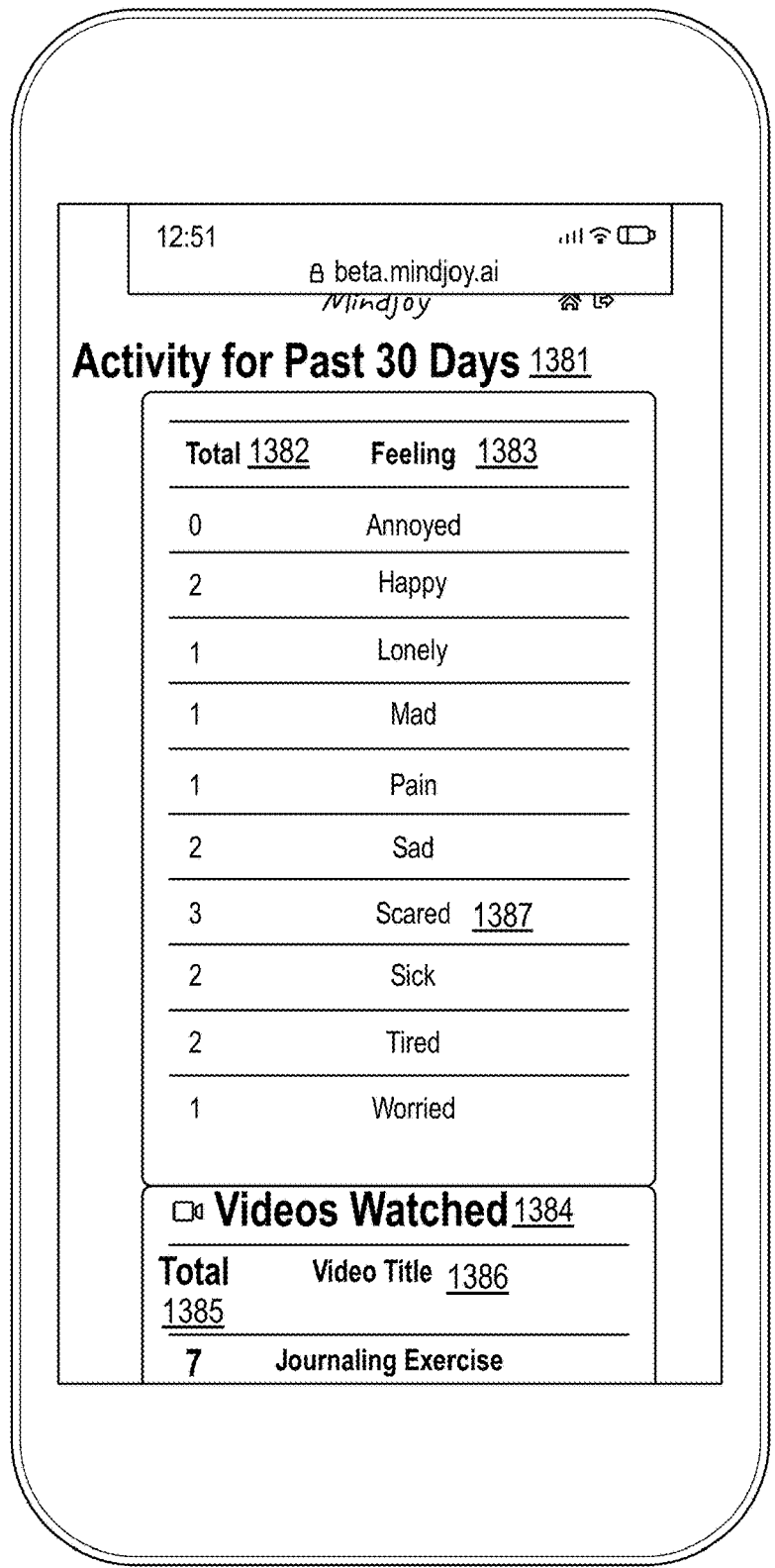

As shown at FIG. 13G, there is an exemplary therapist dashboard view 1380 in which the therapist may view various metrics for their patient, such as the number of times 1382 a given activity occurred within the last specified period of time 1381. Here the therapist is presented with information showing that the child was "scared" 1387 as an indicated feeling 1383 three (3) times within the last 30 days.

Additionally depicted is the quantity of times 1385 the child viewed a particular video content selection 1386 under "videos watched" 1384.

Figure 13H:
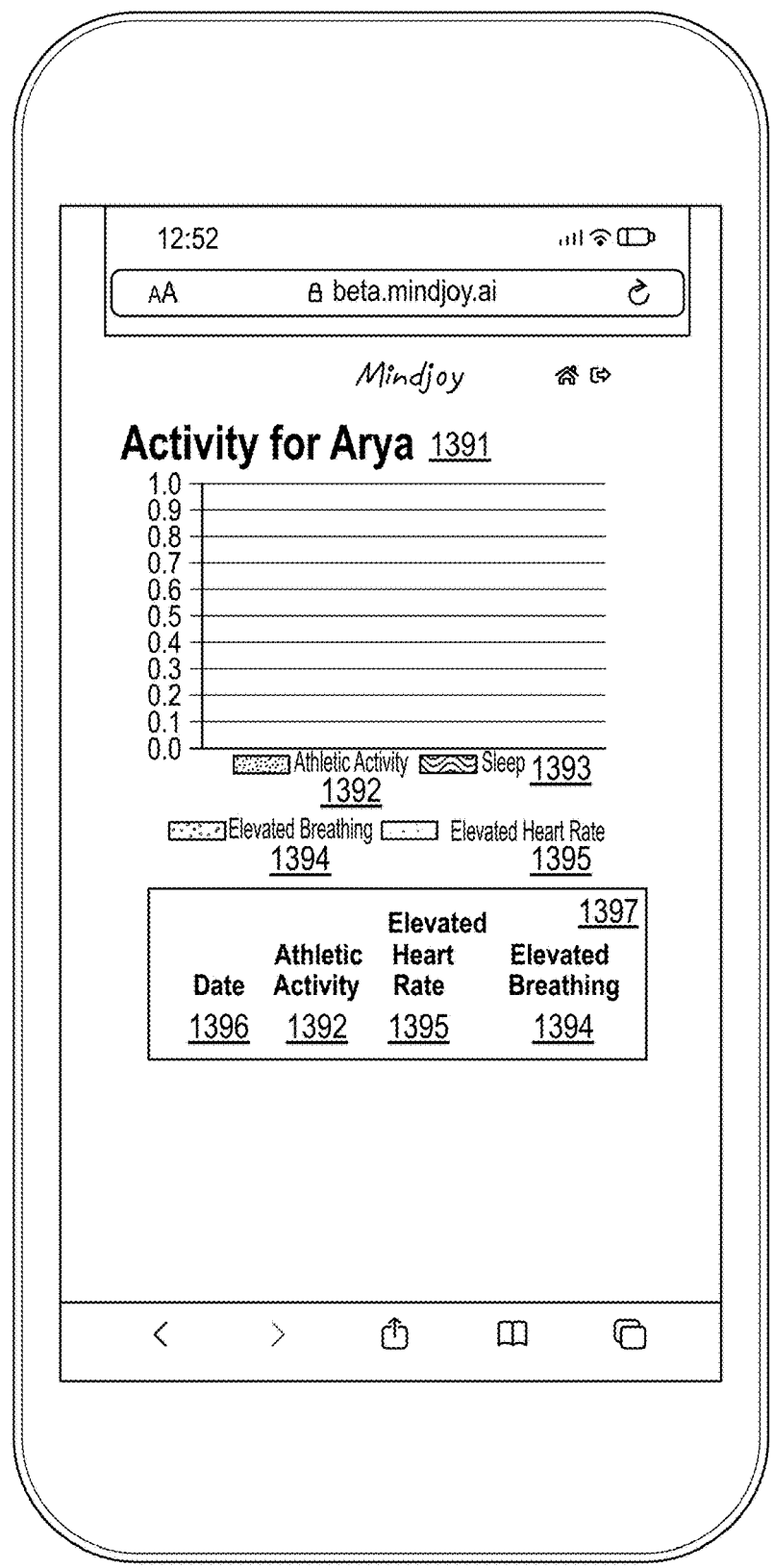

As shown at FIG. 13H, there is an exemplary therapist dashboard view 1390 in which the therapist may observe biometric data 1392-1395 for a given patient. As shown here, data for patient Arya is presented in graph format 1391, for which the various attributes are presented including athletic activity 1392, sleep 1393, elevated breathing 1394, and elevated heart rate 1395, along with a chart view 1397 depicting the number of times each attribute was detected.

FIG. 14 illustrates a diagrammatic representation of a machine 1401 in the exemplary form of a computer system, in accordance with one embodiment, within which a set of instructions, for causing the machine/computer system 1401 to perform any one or more of the methodologies discussed herein, may be executed. In alternative embodiments, the machine may be connected (e.g., networked) to other machines in a Local Area Network (LAN), an intranet, an extranet, or the public Internet. The machine may operate in the capacity of a server or a client machine in a client-server network environment, as a peer machine in a peer-to-peer (or distributed) network environment, as a server or series of servers within an on-demand service environment. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify and mandate the specifically configured actions to be taken by that machine pursuant to stored instructions. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 1401 includes a processor 1402, a main memory 1404 (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), volatile but high-data rate RAM, etc.), and a secondary memory 1418 (e.g., a persistent storage device including hard disk drives and a persistent database and/or a multi-tenant database implementation), which communicate with each other via a bus 1430. Main memory 1404 includes various specialized components and computing architecture circuitry including the Mindjoy platform logic 1424 (e.g., via which therapist settings and child patient interactions may be processed), the dashboard GUI generator 1423 (e.g., via which the Behavioral Health Engagement Platform ("Mindjoy Platform") 299 and associated Mindjoy platform logic 1424 may generate the appropriate child GUI view, parent GUI view, and therapist GUI view, etc.), and the content selector 1425 capable of selecting the appropriate interactive multi-media content for transmission to a child's computing device, all of which is operable in conjunction with the Behavioral Health Engagement Platform ("Mindjoy Platform") 299 for use in promoting child patient engagement with the platform to optimize behavioral and mental health outcomes by processing relevant user input data in support of the methodologies and techniques described herein. Main memory 1404 and its sub-elements are further operable in conjunction with processing logic 1426 and processor 1402 to perform the methodologies discussed herein.

Processor 1402 represents one or more specialized and specifically configured processing devices such as a microprocessor, central processing unit, or the like. More particularly, the processor 1402 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 1402 may also be one or more special-purpose processing devices such as an application-specific integrated circuit (ASIC), a field programmable gate array (FPGA), a digital signal processor (DSP), network processor, or the like. Processor 1402 is configured to execute the processing logic 1426 for performing the operations and functionality which is discussed herein.

The computer system 1401 may further include a network interface card 1408. The computer system 1401 also may include a user interface 1410 (such as a video display unit, a liquid crystal display, etc.), an alphanumeric input device 1412 (e.g., a keyboard), a cursor control device 1413 (e.g., a mouse), and a signal generation device 1416 (e.g., an integrated speaker). The computer system 1401 may further include peripheral device 1436 (e.g., wireless or wired communication devices, memory devices, storage devices, audio processing devices, video processing devices, (Augmented Reality/Virtual Reality (AR/VR) tech, wearables, haptic tech, etc.).

The secondary memory 1418 may include a non-transitory machine-readable storage medium or a non-transitory computer readable storage medium or a non-transitory machine-accessible storage medium 1431 on which is stored one or more sets of instructions (e.g., software 1422) embodying any one or more of the methodologies or functions described herein. The software 1422 may also reside, completely or at least partially, within the main memory 1404 and/or within the processor 1402 during execution thereof by the computer system 1401, the main memory 1404 and the processor 1402 also constituting machine-readable storage media. The software 1422 may further be transmitted or received over a network 1420 via the network interface card 1408.

According to a particular embodiment, there is an integrative behavioral health engagement platform comprising: a memory to store instructions; a processor to execute the instructions at the behavioral health engagement platform; wherein the instructions are configured such that, when executed by the processor of the behavioral health engagement platform, the behavioral health engagement platform carries out operations including: receiving a request at the platform from a therapist user device requesting access to the platform; generating, at the platform, a therapist GUI interface based upon the request; receiving therapist user input at the platform via the therapist GUI interface specifying a diagnostic modality for a patient, wherein content is pre-selected based on the pre-defined diagnostic modality; transmitting the content to a patient GUI interface for display at a patient user device; receiving patient user input at the platform from the GUI interface displayed to the patient user device, wherein the patient user input specifies one or more of: (i) selection of an avatar, (ii) responses to questions about the patient's compliance with treatment, (iii) responses to questions about the patient's emotional state and triggers before and after (iii) the viewing and rating of the pre-selected content, and (iv) biometric feedback from the patient; modifying the pre-selected content including content sequence based upon the patient user input; sending the modified pre-selected content to the patient GUI interface at the patient user device; creating alert notifications at the platform based on one or more of: (i) the patient user input meeting or exceeding pre-set thresholds, and (ii) pre-set time points; sending the alert notification to the therapist GUI interface for display at a therapist user device and a parent GUI interface for display at a parent user device; and monitoring and promoting positive behavioral health outcomes.

Figure 15A:
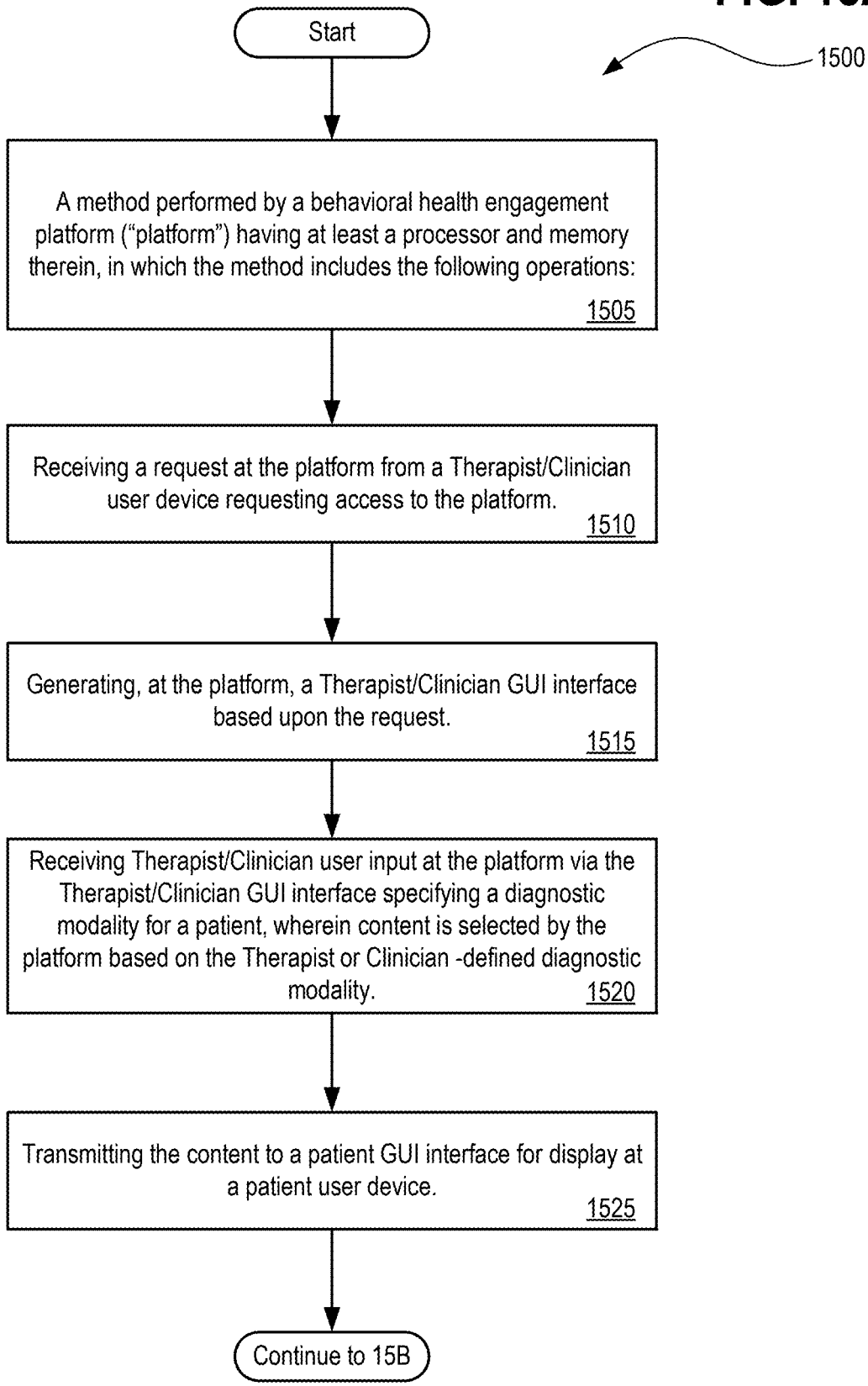

FIGS. 15A and 15B depict flow diagrams illustrating a method 1500 and 1501 for implementing and utilizing a behavioral health engagement platform, in accordance with disclosed embodiments. Method 1500 and 1501 may be performed by processing logic that may include hardware (e.g., circuitry, dedicated logic, programmable logic, microcode, etc.), software (e.g., instructions run on a processing device) to perform various operations such as designing, defining, retrieving, parsing, persisting, exposing, loading, executing, operating, receiving, generating, storing, maintaining, creating, returning, presenting, interfacing, communicating, transmitting, querying, processing, providing, determining, triggering, displaying, updating, sending, etc., in pursuance of the systems and methods as described herein. For example, the machine 1401 (see FIG. 14) and the other supporting systems and components as described herein may implement the described methodologies. Some of the blocks and/or operations listed below are optional in accordance with certain embodiments. The numbering of the blocks presented is for the sake of clarity and is not intended to prescribe an order of operations in which the various blocks must occur.

With reference to the method 1500 depicted at FIG. 15A beginning at block 1505, there is a method performed by a behavioral health engagement platform ("platform") having at least a processor and memory therein, in which the method includes the following operations:

At block 1510, processing logic receives a request at the platform from a therapist user device requesting access to the platform.

At block 1515, processing logic generates, at the platform, a therapist GUI interface based upon the request.

At block 1520, processing logic receives therapist user input at the platform via the therapist GUI interface specifying a diagnostic modality for a patient, wherein content is selected by the platform based on the therapist-defined diagnostic modality.

At block 1525, processing logic transmits the content to a patient GUI interface for display at a patient user device.

Transitioning to the continuation of method 1500, processing advances to FIG. 15B, where method 1501 and specifically block 1530 includes processing logic receives patient user input at the platform from the GUI interface displayed to the patient user device, wherein the patient user input specifies one or more of: (i) selection of an avatar, (ii) responses to questions about the patient's compliance with treatment, (iii) responses to questions about the patient's emotional state and triggers before and after (iii) the viewing and rating of the platform-selected content, and (iv) biometric feedback from the patient.

At block 1535, processing logic modifies the platform-selected content and sequence to be transmitted to the patient user device based upon the patient user input.

At block 1540, processing logic sends the platform-selected content to the patient GUI interface at the patient user device in accordance with the sequence and modifications determined by the platform.

At block 1545, processing logic creates alert notifications at the platform based on one or more of: (i) the patient user input meeting or exceeding pre-set thresholds, and (ii) pre-set time points.

At block 1550, processing logic sends the alert notification to the therapist GUI interface for display at a therapist user device and a parent GUI interface for display at a parent user device.

At block 1555, processing logic monitors and promotes positive behavioral health outcomes via the variously described embodiments.

According to another embodiment, method 1500-1501 further includes:

According to another embodiment of method 1500-1501, the patient is a child, wherein the therapist user device is displayed to a therapist, wherein the patient GUI interface is granted access to the platform via the therapist GUI interface sending an invitation to the parent GUI interface for display at the parent user device, wherein the parent user device is displayed to a parent of the child, wherein parent user input is received at the platform via the parent GUI interface specifying patient user parameters of age, diagnosis and recommended treatment modality, wherein the patient is authenticated based on one or more of (i) age, (ii) diagnosis, (iii) recommended treatment modality, (iv) biometric feedback, and (v) voice and facial recognition. Fore example, through the collection of voice recognition data, the platform implements an automatic mental-health monitor (e.g., via an AI chatbot) to receive, analyze, and respond to the patient based on the human voice for analysis of mental health symptoms. For example, such an AI Chatbot, when used in conjunction with wearables, may thus serve to optimize treatment based on daily application interactions for psychiatric symptom diagnosis+prognosis. According to a particular embodiment, an embodied agent (e.g., via the capture of video, audio, and text) enables the platform to propose multiple modality ML methods for augmenting interactive agents with emotional intelligence so as to assist in mental health assessment which in turn improves prognosis and treatment with automated behavioral analysis. According to another embodiment, interactions with audio/video visual content and questionnaires permits the platform to screen, monitor, and to predict mental health states of the patient based on user response and inputs at the GUI (e.g., displayed to the patient's user device) responsive to questions and emotions recommending content and constructive stress coping mechanisms.

According to another embodiment of method 1500-1501, the biometric feedback includes heart rate, pulse, breathing rate, oxygen saturation, secretions, and sleep cycle information. For instance, collection of oxygen saturation and/or secretions such as human sweat, facilitate the analysis of and ultimately a predictive indication as to the presence of hyperventilation of a child or the sensing and analysis as to the contents of human secretions to make a prediction as to a child's predisposition to certain diseases. More particularly, the system may indicate or diagnose a particular illness or disease based on sensory data and biometric characteristics originating from a smart device showing a high level of certain minerals, such as sodium or potassium, which thus in turn will translate to the likely presence of certain disease modalities.

According to another embodiment of method 1500-1501, the pre-selected content is pre-selected and modified by a machine learning algorithm.

According to another embodiment of method 1500-1501, the biometric feedback received is gyroscopic and minimizes non-behavioral health confounders such as increased heart rate from exercise being misattributed to anxiety or mania.

According to another embodiment of method 1500-1501, the patient selects and views the modified pre-selected content at the patient GUI interface at the patient user device.

According to another embodiment of method 1500-1501, each GUI interface is customized to display select data at each user device.

According to another embodiment of method 1500-1501, points are awarded to the patient based on patient user input, pre-selected content viewed and scoring settings specified, wherein points may be redeemed by the patient for prizes and activities.

According to another embodiment of method 1500-1501, input about the patient is received from subsequent users such as other healthcare providers and school staff, wherein the alert notifications are also sent to GUI interfaces for such users to be displayed at user devices for such users.

According to a particular embodiment, there is a non-transitory computer readable storage media having instructions stored thereupon that, when executed by a behavioral health engagement platform having at least a processor and a memory therein, the instructions cause the behavioral health engagement platform to perform operations including: receiving a request at the platform from a therapist user device requesting access to the platform; generating, at the platform, a therapist GUI interface based upon the request; receiving therapist user input at the platform via the therapist GUI interface specifying a diagnostic modality for a patient, wherein content is selected by the platform based on the therapist-defined diagnostic modality; transmitting the content to a patient GUI interface for display at a patient user device; receiving patient user input at the platform from the GUI interface displayed to the patient user device, wherein the patient user input specifies one or more of: (i) selection of an avatar, (ii) responses to questions about the patient's compliance with treatment, (iii) responses to questions about the patient's emotional state and triggers before and after (iii) the viewing and rating of the platform-selected content, and (iv) biometric feedback from the patient; modifying the platform-selected content and sequence to be transmitted to the patient user device based upon the patient user input; sending the platform-selected content to the patient GUI interface at the patient user device in accordance with the sequence and modifications determined by the platform; creating alert notifications at the platform based on one or more of: (i) the patient user input meeting or exceeding pre-set thresholds, and (ii) pre-set time points; sending the alert notification to the therapist GUI interface for display at a therapist user device and a parent GUI interface for display at a parent user device; and monitoring and promoting positive behavioral health outcomes.

While the subject matter disclosed herein has been described by way of example and in terms of the specific embodiments, it is to be understood that the claimed embodiments are not limited to the explicitly enumerated embodiments disclosed. To the contrary, the disclosure is intended to cover various modifications and similar arrangements as would be apparent to those skilled in the art. Therefore, the scope of the appended claims should be accorded the broadest interpretation so as to encompass all such modifications and similar arrangements. It is to be understood that the above description is intended to be illustrative, and not restrictive. Many other embodiments will be apparent to those of skill in the art upon reading and understanding the above description. The scope of the disclosed subject matter is therefore to be determined in reference to the appended claims, along with the full scope of equivalents to which such claims are entitled.

What is claimed is:

1. A holistic integrated behavioral health engagement platform ("platform"), comprising:
 a memory to store instructions;
 a processor to execute the instructions at the holistic integrated health engagement platform;
 wherein the instructions are configured so that, when executed by the processor of the holistic integrated health engagement platform, the holistic integrated health engagement platform carries out operations including:
 receiving a request at the platform from a therapist/clinician user device requesting access to the platform;
 generating, at the platform, a therapist/clinician GUI interface based upon the request;
 receiving therapist/clinician user input at the platform via the therapist/clinician GUI interface specifying a diagnostic modality for a patient, wherein content is pre-selected based on the pre-defined diagnostic modality;

transmitting the content to a patient GUI interface for display at a patient user device;

receiving patient user input at the platform from the patient GUI interface displayed to the patient user device, wherein the patient user input specifies one or more of: (i) selection of an avatar, (ii) responses to questions about the patient's compliance with treatment, (iii) responses to questions about the patient's emotional state and triggers before and after (iii) the viewing and rating of the pre-selected content, and (iv) biometric feedback from the patient;

modifying the pre-selected content including content sequence based upon the patient user input;

sending the modified pre-selected content to the patient GUI interface at the patient user device;

creating alert notifications at the platform based on one or more of: (i) the patient user input meeting or exceeding pre-set thresholds, and (ii) pre-set time points;

sending the alert notification to the therapist/clinician GUI interface for display at a therapist/clinician user device and a parent GUI interface for display at a parent user device; and iteratively monitoring for and promoting positive behavioral health outcomes via the selection and sending of content to the patient GUI interface at the patient user device based on the patient's emotional state and triggers before and after the viewing and rating of the pre-selected content sent in subsequent iterative rounds.

2. The holistic integrated health engagement platform of claim 1:

wherein the patient is a child, wherein the therapist/clinician user device is displayed to a therapist, wherein the patient GUI interface is granted access to the platform via the therapist/clinician GUI interface sending an invitation to the parent GUI interface for display at the parent user device, wherein the parent user device is displayed to a parent of the child, wherein parent user input is received at the platform via the parent GUI interface specifying patient user parameters of age, diagnosis and recommended treatment modality, wherein the patient is authenticated based on one or more of (i) age, (ii) diagnosis, (iii) recommended treatment modality, (iv) biometric feedback, and (v) facial recognition.

3. The holistic integrated health engagement platform of claim 2:

wherein the biometric feedback includes heart rate, pulse, breathing rate, and sleep cycle information.

4. The holistic integrated health engagement platform of claim 1:

wherein the pre-selected content is pre-selected and modified by a machine learning algorithm.

5. The holistic integrated health engagement platform of claim 1:

wherein the biometric feedback received minimizes non-behavioral health confounders including at least an increased heart rate from exercise being misattributed to anxiety or mania.

6. The holistic integrated health engagement platform of claim 1:

wherein the patient selects and views the modified pre-selected content at the patient GUI interface at the patient user device.

7. The holistic integrated health engagement platform of claim 1:

wherein each GUI interface is customized to display select data at each user device.

8. The holistic integrated health engagement platform of claim 1:

wherein points are awarded to the patient based on patient user input, pre-selected content viewed and scoring settings specified, wherein points may be redeemed by the patient for prizes and activities.

9. The holistic integrated health engagement platform of claim 1:

wherein input about the patient is received from subsequent users such as other healthcare providers and school staff, wherein the alert notifications are also sent to GUI interfaces for such users to be displayed at user devices for such users.

10. A computer-implemented method performed by a holistic integrated health engagement platform ("platform") having at least a processor and memory therein, wherein the method comprises:

receiving a request at the platform from a therapist/clinician user device requesting access to the platform;

generating, at the platform, a therapist/clinician GUI interface based upon the request;

receiving therapist or clinician user input at the platform via the therapist/clinician GUI interface specifying a diagnostic modality for a patient, wherein content is selected by the platform based on the therapist-defined diagnostic modality;

transmitting the content to a patient GUI interface for display at a patient user device;

receiving patient user input at the platform from the patient GUI interface displayed to the patient user device, wherein the patient user input specifies one or more of: (i) selection of an avatar, (ii) responses to questions about the patient's compliance with treatment, (iii) responses to questions about the patient's emotional state and triggers before and after (iii) the viewing and rating of the platform-selected content, and (iv) biometric feedback from the patient;

modifying the platform-selected content and sequence to be transmitted to the patient user device based upon the patient user input;

sending the platform-selected content to the patient GUI interface at the patient user device in accordance with the sequence and modifications determined by the platform;

creating alert notifications at the platform based on one or more of: (i) the patient user input meeting or exceeding pre-set thresholds, and (ii) pre-set time points;

sending the alert notification to the therapist/clinician GUI interface for display at the therapist/clinician user device and a parent GUI interface for display at a parent user device; and iteratively monitoring for and promoting positive behavioral health outcomes via the selection and sending of content to the patient GUI interface at the patient user device based on the patient's emotional state and triggers before and after the viewing and rating of the pre-selected content sent in subsequent iterative rounds.

11. The computer-implemented method of claim 10:

wherein the patient is a child, wherein the therapist/clinician user device is displayed to a therapist, wherein the patient GUI interface is granted access to the platform via the therapist/clinician GUI interface sending an invitation to the parent GUI interface for display at the parent user device, wherein the parent user device is displayed to a parent of the child, wherein parent user input is received at the platform via the parent GUI interface specifying patient user parameters of age, diagnosis and recommended treatment modality, wherein the patient is authenticated based on one or more of (i) age, (ii) diagnosis, (iii) recommended treatment modality, (iv) biometric feedback, and (v) facial recognition; and wherein the biometric feedback includes heart rate, pulse, breathing rate, and sleep cycle information.

12. The computer-implemented method of claim 10:
wherein the pre-selected content is pre-selected and modified by a machine learning algorithm.

13. The computer-implemented method of claim 10:
wherein the biometric feedback received minimizes non-behavioral health confounders including at least an increased heart rate from exercise being misattributed to anxiety or mania.

14. The computer-implemented method of claim 10:
wherein the patient selects and views the modified pre-selected content at the patient GUI interface at the patient user device.

15. The computer-implemented method of claim 10:
wherein each GUI interface is customized to display select data at each user device.

16. The computer-implemented method of claim 10:
wherein points are awarded to the patient based on patient user input, pre-selected content viewed and scoring settings specified, wherein points may be redeemed by the patient for prizes and activities.

17. The computer-implemented method of claim 10:
wherein input about the patient is received from subsequent users such as other healthcare providers and school staff, wherein the alert notifications are also sent to GUI interfaces for such users to be displayed at user devices for such users.

18. Non-transitory computer readable storage media having instructions stored thereupon that, when executed by a holistic integrated health engagement platform having at least a processor and a memory therein, the instructions cause the behavioral health engagement platform to perform operations including:
receiving a request at the platform from a therapist/clinician user device requesting access to the platform;
generating, at the platform, a therapist/clinician GUI interface based upon the request;
receiving therapist or clinician user input at the platform via the therapist/clinician GUI interface specifying a diagnostic modality for a patient, wherein content is pre-selected based on the pre-defined diagnostic modality;
transmitting the content to a patient GUI interface for display at a patient user device;
receiving patient user input at the platform from the patient GUI interface displayed to the patient user device, wherein the patient user input specifies one or more of: (i) selection of an avatar, (ii) responses to questions about the patient's compliance with treatment, (iii) responses to questions about the patient's emotional state and triggers before and after (iii) the viewing and rating of the pre-selected content, and (iv) biometric feedback from the patient;
modifying the pre-selected content including content sequence based upon the patient user input;
sending the modified pre-selected content to the patient GUI interface at the patient user device;
creating alert notifications at the platform based on one or more of: (i) the patient user input meeting or exceeding pre-set thresholds, and (ii) pre-set time points;
sending the alert notification to the therapist/clinician GUI interface for display at the therapist/clinician user device and a parent GUI interface for display at a parent user device; and
iteratively monitoring for and promoting positive behavioral health outcomes via the selection and sending of content to the patient GUI interface at the patient user device based on the patient's emotional state and triggers before and after the viewing and rating of the pre-selected content sent in subsequent iterative rounds.

19. The non-transitory computer readable storage media of claim 18:
wherein the patient is a child, wherein the therapist/clinician user device is displayed to a therapist or clinician, wherein the patient GUI interface is granted access to the platform via the therapist/clinician GUI interface sending an invitation to the parent GUI interface for display at the parent user device, wherein the parent user device is displayed to a parent of the child, wherein parent user input is received at the platform via the parent GUI interface specifying patient user parameters of age, diagnosis and recommended treatment modality, wherein the patient is authenticated based on one or more of (i) age, (ii) diagnosis, (iii) recommended treatment modality, (iv) biometric feedback, and (v) facial recognition; and
wherein the biometric feedback includes heart rate, pulse, breathing rate, and sleep cycle information.

20. The non-transitory computer readable storage media of claim 18:
wherein the biometric feedback received minimizes non-behavioral health confounders including at least an increased heart rate from exercise being misattributed to anxiety or mania.

\* \* \* \* \*